US005693296A

United States Patent [19]
Holtzapple et al.

[11] Patent Number: 5,693,296
[45] Date of Patent: Dec. 2, 1997

[54] CALCIUM HYDROXIDE PRETREATMENT OF BIOMASS

[75] Inventors: Mark T. Holtzapple, College State; Richard R. Davison, Bryan; Murlidhar Nagwani, Houston, all of Tex.

[73] Assignee: The Texas A&M University System, College Station, Tex.

[21] Appl. No.: 300,543

[22] Filed: Sep. 6, 1994

Related U.S. Application Data

[63] Continuation-in-part of Ser. No. 926,739, Aug. 6, 1992, abandoned.

[51] Int. Cl.$^6$ .......................... C01F 11/02; C01F 11/06; A23K 1/12
[52] U.S. Cl. .................. 423/165; 426/635; 426/636; 127/37
[58] Field of Search .................. 536/56, 124; 162/29, 162/90, 190; 530/500; 426/312, 635, 636; 127/37; 423/165

[56] References Cited

U.S. PATENT DOCUMENTS

| | | |
|---|---|---|
| 3,212,933 | 10/1965 | Hess et al. . |
| 3,639,206 | 2/1972 | Spruill .................................. 162/29 |
| 3,707,436 | 12/1972 | O'Connor . |
| 3,875,317 | 4/1975 | Ferguson . |
| 3,944,463 | 3/1976 | Samuelson et al. . |
| 4,087,317 | 5/1978 | Roberts . |
| 4,113,553 | 9/1978 | Samuelson . |
| 4,356,196 | 10/1982 | Hultquist . |
| 4,597,830 | 7/1986 | April et al. . |
| 4,842,877 | 6/1989 | Tyson . |
| 5,198,074 | 3/1993 | Villavicencio et al. . |

FOREIGN PATENT DOCUMENTS

| | | |
|---|---|---|
| 8207036 | 12/1982 | Brazil . |
| 0045500 | 2/1982 | European Pat. Off. . |
| 58-098093 | 6/1983 | Japan . |

OTHER PUBLICATIONS

Iwata "The Simple Method of Straw Disintigration", Nippon Chikusan Gakkai Ho, pp. 189–199 (1930).
Negi et al. "Digestibility of Carbohydrates in Terms of the Conventional Vis a Vis the Newer Fractions in Untreated and Treated Paddy Straw Rations," The India–Veterinary Journal, v. 40, Nov. 1963, pp. 718–724.
Maeng et al. "Improving the Nutritive Value of Rice Straw I. Effect of Alkali Treatment on the Chemical Composition and in Vitro Digestibility of India Type Rice Straw", Hanguk Ch'uksan Hakhoe Ch: (1979), 21(4), 343–9.
Shah et al. "Digestibility of Alkali Treated Corn Cobs", Pak. J. Sci. Ind. Res. (1992), 35(4), 126–30.
Winugroho et al. "A Soak and Press Method for the Alkali Treatment of Fibrous Crop Residues", Agricultural Wastes 9 (1984) 87–99.
Iwata, Translation of "Sample Methods for Rice Straw Disintigration", Journal of the Japanese Livestock Society pp. 189–199 (1930).
Shah et al. "Digestibility of Some Crop Residues After Steam/Pressure Treatments" Biol. Wastes (1987), 19(1), 63–67.
Playne "Increased Digestibility of Bagasse by Pretreatment with Alkalis and Steam Explosion", Biotechnol. and Bioeng. vol. XXVI, 26, 426–433 (1984).
Vinod P. Puri, "Effect of Crystallinity and Degree of Polymerization of Cellulose on Enzymatic Saccharification," *Biotechnology and Bioengineering*, vol. XXVI, pp. 1219–1222, (1984).
M. A. Millett et al., "Modifying Wood to Increase Its In Vitro Digestibility," *Journal of Animal Science*, vol. 31, No. 4, pp. 781–788, Oct. 1970.
Wayne E. Moore et al., "Hydrolysis of Wood and Cellulose with Cellulytic Enzymes," *J. Agr. Food Chem.*, vol. 20, No. 6, pp. 1173–1175, (1972).
A. C. Waiss, Jr., "Improving Digestibility of Straws for Ruminant Feed by Aqueous Ammonia," *Journal of Animal Science*, vol. 35, No. 1, pp. 109–112, (1972).
P. J. Morris et al., "Nutritive Value of Ground And/Or Ammoniated Corn Stover," *Can. J. Anim. Sci.*, vol. 60, No. 2, pp. 327–336, (Jun. 1980).
Merill A. Millett et al., "Pretreatments to Enhance Chemical, Enzymatic, and Microbiological Attack of Cellulosic Materials," *Biotechnol. & Bioeng. Symp.*, No. 5, pp. 193–219, (1975).
R. W. Mellenberger et al., "Digestion of Aspen, Alkali–Treated Aspen, and Aspen Bark by Goats," *Journal of Animal Science*, vol. 32, No. 4, pp. 756–763, (Apr. 1971).
Harry Schleicher et al., "Changes of Cellulose Accessibility to Reactions in Alkaline Medium by Activation with Ammonia," *Journal of Polym. Sci. Symp.*, vol. 47, pp. 251–260, (1974).
A. Felix et al., "In Vitro and In Vivo Digestibility of Soya–Beam Straw Treated with Various Alkalis," *Animal Prod.*, 1990, 51, 47.

(List continued on next page.)

*Primary Examiner*—Jeffrey C. Mullis
*Attorney, Agent, or Firm*—James Remenick; Baker & Botts, L.L.P.

[57] ABSTRACT

Lignocellulose-containing materials are treated with lime (calcium hydroxide) and water at a relatively high temperature and for a certain period of time under certain conditions. The process variables were: lime loading which ranged from about 2 to about g Ca(OH)$_2$/100 g dry material; water loading which ranged from about 6 to about 19 g water/g dry material; treatment temperature which varied from about 50° C. to about 150° C.; and treatment time which varied from about 1 to about 36 hours. The effects of treatment time and temperature were interdependent.

A process for lime recovery is developed. The soluble Ca(OH)$_2$ was washed out of the pretreated material with water and converted to insoluble CaCO$_3$, by reacting with CO$_2$, and was thus separated. The CaCO$_3$ can be heated to produce CaO and CO$_2$. The CaO is hydrated to Ca(OH)$_2$ which can be reused as the lignocellulose treatment agent. Carbon dioxide is reused for lime recovery.

30 Claims, 9 Drawing Sheets

OTHER PUBLICATIONS

John C. Waller et al., "Hydroxides for Treating Crop Residues," *Journal of Animal Science*, vol. 41, pp. 424–425, Abstract 711, (1975).

D. Craig Anderson et al., "Chemical Treatment of Ryegrass Straw: In Vitro Dry Matter Digestibility and Compositional Changes," *Journal of Animal Science*, vol. 37, No. 1, pp. 148–152, (1973).

P. H. Robinson et al., "Influence of Ammoniation of High Moisture Barley On Its In Situ Rumen Degradation and Influence on Rumen Fermentation in Dairy Cows," *Can. J. Anim. Sci.*, vol. 68, pp. 839–851, (Sep. 1988).

Harold Tarkow et al., "A Mechanism for Improving the Digestibility of Lignocellulosic Materials with Dilute Alkali and Liquid Ammonia," *ACS*, 95, pp. 197–217, (1969).

Josef Schurz, "How to Make Native Lignocellulosic Materials Accessible to Chemical and Microbial Attack," *Proc. Bioconversion Symp., IIT Delhi*, pp. 37–58, (1977).

Terry Klopfenstein, "Chemical Treatment of Crop Residues," *Journal of Animal Science*, vol. 46, No. 3, pp. 841–848, (1978).

F. H. Gharib et al., "In Vitro Evaluation of Chemically–Treated Poplar Bark," *Journal of Animal Science*, vol. 40, No. 4, pp. 734–742, (1975).

B. S. Capper et al., "Alkali–Treated Roughages for Feeding Ruminants: A Review," *Trop. Sci.*, vol. 19, No. 2, pp. 73–87, (1977).

600I Chemical Abstracts, vol. 93, No. 17, Oct. 27, 1980, 93:166609a, p. 539.

600I Chemical Abstracts, vol. 100, No. 17, Apr. 1984, 137872p, p. 544.

CALCIUM HYDROXIDE PRETREATMENT OF BIOMASS

REFERENCE TO RELATED APPLICATIONS

This is a continuation-in-part of U.S. patent application Ser. No. 07/926,739, filed Aug. 6, 1992, now abandoned.

BACKGROUND OF THE INVENTION

1. Field of the Invention

The present invention relates to pretreating lignocellulose-containing materials with a certain amount of lime and water at a relatively high temperature for a certain period of time to render the material amenable to enzymatic digestion and also relates to recovering the lime from the mixture.

2. Description of the Background

Biomass can be classified in three main categories: sugar-, starch- and cellulose-containing plants. Sugar-containing plants (e.g. sweet sorghum, sugarcane) and starch-containing plants (e.g. corn, rice, wheat, sweet potatoes) are primarily used as food sources. Cellulose-containing plants and waste products (e.g. grasses, wood, bagasse, straws) are the most abundant forms of biomass. Although they are not easily converted to useful products, a well engineered process to convert them to feedstock may potentially be economical since the costs of feedstock are much less than those of sugar and starch-containing biomass.

Cellulose-containing materials are generally referred to as lignocellulosics because they contain cellulose (40%–60%), hemicellulose (20%–40%) and lignin (10%–25%). Non-woody biomass generally contains less than about 15–20% lignin. Cellulose, a glucose polymer, can be hydrolyzed to glucose using acid, enzymes or microbes. Glucose can serve as a feedstock for fuel alcohol and single-cell protein production. Microbial hydrolysis produces cellular biomass (i.e. single-cell protein) and metabolic waste products such as organic acids. Acid hydrolysis, although simple, produces many undesirable degradation products. Enzymatic hydrolysis is the cleanest and most preferred approach. However, production of enzymes, mainly cellulase and cellobiase, can be an expensive step. Apart from alcohol production, lignocellulose can be used as inexpensive cattle feed. Since raw lignocellulose cannot be easily digested by cattle, it must be processed to improve its digestibility before it can be fed to ruminants. Also, anaerobic fermentation using rumen microorganisms can produce low molecular weight volatile fatty acids.

Cellulose is the world's most abundant biological material. Approximately 40% to 45% of the dry weight of wood species is cellulose. The degree of polymerization ranges from 500 to 20,000. Cellulose molecules are completely linear, unbranched and have a strong tendency to form inter- and intra-molecular hydrogen bonds. Bundles of cellulose molecules are thus aggregated together to form microfibrils in which highly ordered (crystalline) regions alternate with less ordered (amorphous) regions. Microfibrils make fibrils and finally cellulose fibers. As a consequence of its fibrous structure and strong hydrogen bonds, cellulose has a very high tensile strength and is insoluble in most solvents.

Hemicellulose is the world's second most abundant carbohydrate and comprises about 20% to 30% of wood dry weight. Hemicelluloses, although originally believed to be intermediates in cellulose biosynthesis, are formed through biosynthetic routes different from cellulose. Hemicelluloses are heteropolysaccharides and are formed by a variety of monomers. The most common monomers are glucose, galactose and mannose (the hexoses) and xylose and arabinose (the pentoses). Most hemicelluloses have a degree of polymerization of only 200. Hemicelluloses can be classified in three families, xylans, mannans and galactans, named for the backbone polymer.

Lignin is the world's most abundant non-carbohydrate biomaterial. It is a three dimensional macromolecule of enormously high molecular weight. Since its units are extensively cross-linked, it is difficult to define an individual molecule. Lignin provides strength by binding cellulose fibrils together. Being hydrophobic in nature, it prevents water loss from the vascular system and, being highly resistant to enzymatic degradation, it protects plants from insects and microbial attack.

Phenylpropane, an aromatic compound, is the basic structural unit of lignin. The monomers not only cross-link with each other, but also covalently bond to hemicellulose. A great constraint to cellulose and hemicellulose accessibility is the presence of lignin. It has been shown that decreased lignin content causes increased digestibility. Lignin can be removed by physical, chemical, or enzymatic treatments. It must be decomposed to smaller units that can be dissolved out of the cellulose matrix. There are several well developed pulping methods that disintegrate and remove lignin, leaving the cellulose fairly intact. Conventional pulping processes, such as Kraft and sulfite pulping, are too costly as bioconversion pretreatments. Also, economical use of the removed lignin is difficult because its chemical structure and size distribution are highly heterogeneous.

Another major deterrent to enzymatic cellulosic hydrolysis is the highly ordered molecular packing of its crystalline regions. Cellulolytic enzymes readily degrade the more accessible amorphous portions of cellulose, but are unable to attack the less accessible crystalline material. Thus, enzymatic hydrolysis rates increase with decreasing crystallinity index measured by X-ray diffraction methods.

The moisture content of cellulose fibers influences enzymatic degradation. Cellulosic materials are effectively protected from deterioration by enzymes or microbes provided the moisture content is maintained below a critical level characteristic of the material and the organism involved. In general, this critical level is slightly above the fiber saturation point, approximately 40% of dry weight. Moisture plays three major roles: (1) it swells the fibers by hydrating cellulose molecules, thus opening up the fine structure and increasing enzyme access, (2) it provides a diffusion medium for enzymes and for partial degradation products, and (3) it is added to cellulose during hydrolytic cleavage of the glycosidic links of each molecule.

The surface area of lignocellulose is another important factor that determines susceptibility to enzymatic degradation. It is important because contact between enzyme molecules and the cellulose surface is a prerequisite for hydrolysis to proceed.

A few other factors that also influence susceptibility include size and diffusibility of enzyme molecules in relation to size and surface properties of capillaries, unit cell dimensions of cellulose molecules, and conformation and steric rigidity of anhydro-glucose units.

To enhance susceptibility to enzymatic hydrolysis, lignocellulose pretreatment is an essential requirement. The heterogeneous enzymatic degradation of lignocellulosics is primarily governed by its structural features because (1) cellulose possesses a highly resistant crystalline structure, (2) the lignin surrounding the cellulose forms a physical barrier and (3) the sites available for enzymatic attack are limited. An ideal pretreatment, therefore, would reduce lignin content, with a concomitant reduction in crystallinity and increase in surface area. Pretreatment methods can be classified into physical, chemical, physicochemical, and biological, depending on the mode of action. The literature available on this subject is voluminous. The various pretreatment methods that have been used to increase cellulose digestibility are summarized in Table 1.

TABLE 1

Methods Used for the Pretreatment of Lignocellulosics.

| Physical | Physicochemical | Biological |
|---|---|---|
| Ball-milling | Steam explosion | Fungi |
| Two-roll milling | Ammonia Fiber Explosion | |
| Hammer milling | | |
| Colloid milling | | |
| High pressure steaming | | |
| High energy radiation | | |
| Pyrolysis | | |

| Chemical | | | |
|---|---|---|---|
| Alkali | Acid | Gas | Oxidizing Agents |
| Sodium Hydroxide | Sulfuric Acid | Chlorine Dioxide | Hydrogen Peroxide |
| Calcium Hydroxide | Hydrochloric Acid | Nitrogen Dioxide | Ozone |
| Ammonia | Hydrofluoric Acid | | |
| Cellulose solvents | Solvent extraction | | |
| | Ethanol-water extraction | | |
| | Benzene-ethanol extraction | | |

Biological Pretreatments: Biological pretreatments employ fungi for microbial de-lignification to make cellulose more accessible. Major biological lignin degraders are the higher fungi, Ascomycetes and Basidiomycetes. Fungal degradation is a slow process and most fungi attack not only lignin, but cellulose also, thus resulting in a mixture of lignin fragments and sugars. Improvements may require developing more specific and efficient microbes.

Physical Pretreatments: Physical pretreatments can be classified in two general categories: mechanical (involving all types of milling) and nonmechanical (involving high-pressure steaming, high energy radiation and pyrolysis). During mechanical pretreatments, physical forces, (e.g. shearing, compressive forces) subdivide lignocellulose into finer particles. These physical forces reduce crystallinity, particle size and degree of polymerization and increase bulk density. These structural changes result in a material more susceptible to acid and enzymatic hydrolysis. However, due to enormously high operating costs associated with the high energy requirements, low yields and large time requirements, these mechanical pretreatments are not practical. Nonmechanical physical pretreatment methods also increase digestibility, but have similar disadvantages and thus are not economical for real processes.

Physicochemical Pretreatments: Steam explosion and Ammonia Fiber Explosion (AFEX) are the main physicochemical pretreatments. Steam explosion heats wetted lignocellulose to high temperatures (about 250° C.) and releases the pressure instantly. Due to rapid decompression, which flashes the water trapped in fibers, physical size reduction occurs. The high temperatures remove acetic acid from hem/cellulose, so this process results in some autohydrolysis of the biomass. These changes result in better digestibilities, but the severe conditions also produce degradation products that inhibit hydrolysis and fermentation. These products are removed by washing with water which results in a loss of water soluble hemicellulose. Thus, although digestibilities are improved, biomass degradation and protein denaturization limits the use of steam explosion.

The AFEX pretreatment process soaks lignocellulose in liquid ammonia at high pressure and then explosively releases the pressure. Pretreatment conditions (30° C.–100° C.) are less severe than steam explosion. An increase in accessible surface area coupled with reduced cellulose crystallinity (caused by ammonia contacting) result in increased enzymatic digestibility. However, use of ammonia (a hazardous chemical) and the high pressure release makes the process quite complex and energy intensive.

Chemical Pretreatments: Many chemical pretreatments have been extensively used for lignin removal and destruction of the lignin crystalline structure. The traditional pulping processes used by the paper industry are quite severe and too expensive for lignocellulose pretreatment. Many researchers have conducted studies with various chemical pretreatment agents such as those listed in Table 1. Of these chemicals, acids, gases, oxidizing agents, cellulose solvents, and solvent extraction agents, are all able to increase digestibility, but are not as popular as alkalis. Economics, simpler processes and less degradation favor alkalis as chemical pretreatment agents. However, most of these are process for paper pulping and involves the complete or nearly complete destruction of lignin, and a corresponding destruction of cellulose. Although unimportant in pulping, these pulping process are quite severe and not useful as pretreatments for biomass. Furthermore, the traditional pulping processes used by the paper industry are too expensive as lignocellulose pretreatment methods.

U.S. Pat. No. 4,644,060 to Chou is directed to the use of super-critical ammonia to increase lignocellulose digestibility.

U.S. Pat. Nos. 4,353,713 and 4,448,588 to Cheng are directed to the gasification of biomass or coal which is an endothermic process. These patents also relate to a method for adding the required thermal energy by reacting lime with carbon dioxide which is an exothermic reaction.

U.S. Pat. No. 4,391,671 to Azarniouch is directed to a method for calcining calcium carbonate in a rotary kiln. The reference specifically relates to the paper/pulp industry where the calcium carbonate would be contaminated with waste biomass. The waste biomass is burned to provide the needed heat of reaction.

U.S. Pat. No. 4,356,196 to Hulquist is directed to treating biomass with ammonia.

U.S. Pat. No. 4,227,964 to Kerr is directed to the use of ammonia to promote the kinking of pulp fiber to increase paper strength, not to break down the fibers.

U.S. Pat. No. 4,087,317 to Roberts is directed to the use of lime and mechanical beating to convert pulp into a hydrated gel. There is no mention of lime recovery or enzymatically hydrolyzing the hydrated gel.

U.S. Pat. No. 4,064,276 to Conradsen is directed to a process where biomass is covered with a tarp and then ammoniated with ammonia, which is allowed to dissipate into the atmosphere.

U.S. Pat. No. 3,939,286 to Jelks is directed to oxidizing biomass with high-pressure oxygen under elevated temperature and pressure in the presence of an acid catalyst, acetic acid and a metal catalyst, ferric chloride, to break lignin bonds and to increase digestibility. The catalysts are described as essential to the process and calcium hydroxide is utilized as a neutralizing agent to adjust the resulting pH of the hydrolyzed biomass.

U.S. Pat. No. 3,878,304 to Moore is directed to production of slow-release nonprotein nitrogen in ruminant feeds. An amide, urea, is reacted with waste carbohydrates in the presence of an acid catalyst. The resulting material is pelleted and used as animal feed. Since the nitrogen is released slowly in the rumen, it is nontoxic to the animal.

U.S. Pat. No. 3,944,463 to Samuelson et al. is directed to a process for producing cellulose pulp of high brightness. The cellulose is pretreated with an alkaline compound at a temperature of between about 60° C. to about 200° C. so as to dissolve between 1 and 30% of the dry weight of the material in the pretreatment liquor. The pretreatment liquor preferably contains sodium carbonate, sodium bicarbonate or mixtures thereof, or possible sodium hydroxide.

U.S. Pat. No. 3,639,206 to Spruill is directed to the treatment of waste water effluent derived from a pulping process with calcium oxide or hydroxide to reduce the fiber and color content of the effluent.

U.S. Pat. No. 4,048,341 to Lagerstrom et al. is directed to a process for increasing the feed value of lignocellulosic material by contacting the material with an alkaline liquid, specifically, sodium hydroxide. The alkaline liquid, supplied in excess, is allowed to run off the material before any essential alkalization effect has been reached. After the liquid absorbed in the material has provided its effect, an acid solution is added to the material to neutralize the excess alkali. The reference does not disclose the interrelationship of temperature and time of alkali treatment, nor does it disclose the optimal amounts of the sodium hydroxide and water.

U.S. Pat. No. 4,182,780 to Lagerstrom et al. is directed to a process for increasing the feed value of lignocellulosic materials by alkali treatment and subsequent neutralization of the materials with an acid in a closed system under circulation of the treating agents.

U.S. Pat. No. 4,515,816 to Anthony is directed to a process in which lignocellulose is treated with dilute acid in an amount of about 1.5 to 2.5% of the dry weight of lignocellulose. The mixture is then stored at ambient conditions for 5 to 21 days in an air-free environment.

U.S. Pat. No. 4,842,877 to Tyson is directed to a process for the delignification of non-woody biomass (<20% lignin). In this process, non-woody biomass is treated with a chelating agent, to prevent unnecessary oxidation, and maintained at high pH and high temperatures (150° F. to 315° F.) in the presence of hydrogen peroxide and pressurized oxygen. Hydrogen peroxide is stated to cause a reaction on the cell walls to allow the hemicellulose and lignin to solubilize and be removed through a subsequent hydrolysis process. Oxygen is added to initiate and accelerate the activation of hydrogen peroxide.

The conditions and results of studies reported in the literature using ammonia (gaseous, anhydrous liquid, or NH4OH) and sodium hydroxide as pretreatment agents are listed in Table 2 and Table 3, respectively. The literature available on the use of these two chemicals to enhance lignocellulose digestibility of ruminant feeds, as well as for hydrolysis to glucose, is extensive. The literature on calcium hydroxide pretreatment processes is considerably less compared to that for sodium hydroxide and ammonia. The conditions and results of studies reported in the literature using calcium hydroxide are shown in Table 4.

TABLE 2

Reported Ammoniation Conditions

| Reference | Type of Biomass | Ammonia State | Temp. (°C.) | Time | Pressure | Particle Size | gNH$_3$/kg dry biomass | Effect on Digestibility |
|---|---|---|---|---|---|---|---|---|
| Villareal 1988 | Coastal Bermuda grass | Gaseous | ambient | — | atmosp. | — | 40 | Increase in DII, CP[1] |
| Waiss et al. 1972 | Rice straws | NH$_4$OH | 160 | 1 h | — | 0.64 cm | 26/52 | Increased[2] |
| Waiss et al. 1972 | Rice straws | NH$_4$OH | ambient | 30 d | atmosp. | 0.64 cm | 50 | Increased[1] |
| Millet et al. 1970 | Aspen sawdust | Liquid | 30/60/90 | 1 h | 155/360/725 psi | — | — | Increased by 51%[2] |
| Millet et al. 1970 | Aspen sawdust | Gaseous | 30 | ½ to 74 h | 155 psi | — | — | Increased by 47%[2] |
| Brown 1987 | Limpo grass | Gaseous | ambient | 30 d | atmosp. | 2.5 cm | 20/30/40 | Increased[1] |
| Kellens et al. 1983 | Wheat straw | NH$_4$OH | 29 | 21 d | atmosp. | 2 mm | 50 | Increased 13% to 33%[2] |
| Kellens et al. 1983 | Wheat straw | Gaseous | 6 | 44 d | atmosp. | 2.5 cm | 50 | Increased[1] |
| Hultquist 1982 | Alfalfa | Liq./Gas. | 20–30 | 30 m | 70–165 psig | 1/16–½ in. | 5/20 | Increased by 50%[2] |
| Millet et al. 1975 | Aspen sawdust | Gaseous | — | 2 h | 70 psi | — | — | Increased by 46%[1] |
| Morris et al. 1980 | Corn stover | — | ambient | — | atmosp. | 1.3 cm | 30 | Increase in DII, DE[1] |

DII = daily intake, CP = crude protein, DE = digestible energy, [1]in vivo, [2]in vitro

TABLE 3

Reported NaOH Treatment Conditions

| Reference | Type of Biomass | Temp. (°C.) | Time | Particle Size | g NaOH/100 g solution | g NaOH/100 g biomass | Effect on Digestibility |
|---|---|---|---|---|---|---|---|
| Moore et al. 1972 | Cotton linters | 30 | 1 h | 40 mesh | 1 | 20 | No effect[2] |
| Moore et al. 1972 | Aspen | 30 | 1 h | 40 mesh | 1 | 20 | Increased from 10% to 50%[2] |
| Millet et al. 1970 | Different wood samples | 25 | 1 h | — | 1 | 20 | Increased[2] |
| Fient et al. 1970 | Different wood samples | 25 | 1 h, 2 h | 40 mesh | 0.5, 1 | 2–20 | Increased[2] |
| Baker et al. 197570 | Aspen sawdust | ambient | 2 h | 0.16 cm | 0.5 | 5 | Increased from 41% to 52%[1] |
| Anderson et al. 1973 | Ryegrass straw | ambient | 24 h | 2.54 cm | 0.5–8 | 7.5–120 | Increased from 33% to 90%[2] |
| Mandels et al. 1974 | Bagasse | 72 | 1 h | ⅛" mesh | 2 | — | Increased[2] |
| Mandels et al. 1974 | Newspaper | 70 | 90 m | ⅛" mesh | 2 | 100 | Increased[2] |
| Turner et al. 1990 | Different grass samples | — | 48 m | 4 mm | 3 | — | Increased[2] |

[1]In vivo, [2]In vitro

TABLE 4

Reported Ca(OH)₂ Treatment Conditions

| Reference | Type of Biomass | Temp. (°C.) | Time | Particle Size | g water/g solution | g Ca(OH)$_2$/100 g biomass | Effect on Digestibility |
|---|---|---|---|---|---|---|---|
| Playne 1984 | Bagasse | 20 | 8 d | 2.25 | 0.87 | 12 to 30 | Increased from 19% to 72%[2] |
| Waller et al. 1975 | Corn cobs | ambient | 14 d | Ground | 0.6 | 4 | Improved digestibility[1] |
| Rounds et al. 1974 | Corn cobs | — | — | — | — | 4 | No effect[2] |
| Gharib et al. 1975 | Poplar bark | ambient | 1 or 150 d | 9.5 mm | 0.6 | 4 to 16 | Increased from 30% to 52%[2] |
| Felix et al. 1990 | Soyabean straw | ambient/frozen | 30 d | Chopped | 0.65 | 2 to 5 | No effect[1] |

[1]In vivo, [2]In vitro

Playne (1984) investigated the effects of alkali treatment and steam explosion on bagasse digestibility. The digestibility of untreated bagasse was 190 g organic matter (OM) /kg bagasse dry matter. It was raised to: 733 g organic matter by using NaOH (and also by using Ca(OH)$_2$ with Na$_2$CO$_3$); to 430 g OM using NH$_3$; and to 724 g OM using Ca(OH)$_2$. When Ca(OH)$_2$ alone was used, a high loading (about 180–300 g Ca(OH)$_2$ kg bagasse) was used. Gharib et at. (1975) used calcium oxide for in vitro evaluation of chemically treated poplar bark. They reported that calcium oxide increased in vitro true digestibility from 38% to 52% for a 150-day treatment, although little improvement was found for a 1-day treatment. Rounds and Klopfenstein (1974) studied the effects of NaOH, KOH. NH$_4$OH and Ca(OH)$_2$ on in vivo digestibility of corn cobs by feeding to lambs and on in vitro digestibility using an artificial rumen. Ca(OH)$_2$ alone was unable to increase the in vitro digestibility, although rations treated with Ca(OH)$_2$+NaOH resulted in higher daily gain and feed efficiency for lambs. Waller and Klopfenstein (1975) used various combinations of NaOH, Ca(OH)$_2$ and NH$_4$OH for treating feed for lambs and heifers and reported that the highest daily gain and lowest feed/gain was obtained for the 3% NaOH+1% Ca(OH)$_2$ rations. Darwish and Galal (1975) used maize cobs treated with 1.5% Ca(OH)$_2$ in a milk production ration and found no significant change in milk output. Felix et al. (1990) evaluated the effects of ensiling and treating soya-bean straw with NaOH, Ca(OH)$_2$ and NH$_4$ OH on ruminant digestibility. Results indicate that there was no significant improvement due to alkali treatment of dry and unensiled straw, although alkali treatment improved digestibility of ensiled straw.

In all of the above studies, there was no significant difference between the digestibility results obtained from Ca(OH)$_2$ pretreated material and those obtained from NH$_3$ or NaOH pretreated material. However, as indicated by most researchers, Ca(OH)$_2$ is much cheaper than other alkalis and potentially may result in an economical pretreatment process. Also, calcium hydroxide is safer to handle and, unlike the sodium residue, the calcium reside is little or no problem for animal feed. Also, when producing calcium acetate using an artificial rumen, using calcium hydroxide as the lignocellulose pretreatment agent will be very economic because the calcium hydroxide needed to neutralize the organic acids works for pretreatment also. However, in all cases, calcium hydroxide did not function as effectively as other chemicals such as sodium hydroxide or ammonia, and considerably less work has been done employing calcium hydroxide compared to other alkalis (T. Klopfenstein, J. Anim. Sci. 48(3):841–48, 1978).

Most of the previous work has been performed by animal scientists trying to develop a very simple process to increase the lignocellulose digestibility of animal feed. All these studies were done at room temperature or below, at lower water loadings, for very long periods and without any mixing. Since the reactors must be fairly large, these long treatment periods are very expensive. In addition, this research is directed toward removal of increasing amounts of lignin from biomass because it is believed that removal of lignin is required to increase digestibility. Consequently, the very first step in traditional pretreatment methods is the removal of lignin (J. Schurtz, Proc. Bioconversion Symp. IIT Delhi, 37–58, 1977). Numerous researchers have documented a direct, inverse relationship between digestibility and lignin content (M. A. Millett et al., Biotechnol. & Bioeng. Symp. No. 5:193–219, 1975; W. C. Feist et al., *J. Anim. Sci.* 30:832, 1970). F. Kong et al. (Appl. Biochem. Biotechnol. 34/35:23–35, 1992) demonstrates that removal of the acetyl groups from lignin increases sugar yields, but also that sugar yields are highest at a final lignin content of about 3.4%. Thus, as in the paper pulping industry, the primary focus of current research on increasing the digestibility of biomass is directed to the complete or nearly complete removal of lignin, and typically hemicellulose as well, from the biomass.

SUMMARY OF THE INVENTION

It is an object of the invention to develop an economical process for calcium hydroxide pretreatment of lignocellulose-containing material.

It is another object of the invention to optimize the pretreatment conditions for lignocellulose-containing material.

It is another object of the invention to develop a calcium hydroxide recovery process.

It is another object of the invention to provide a process for treating a lignocellulose-containing material to render it amenable to enzymatic digestion comprising: adding a sufficient amount of lime and a sufficient amount of water to the lignocellulose-containing material; mixing the lime, water, and lignocellulose-containing material to form a wet mixture; heating the wet mixture to a temperature of from about 40° C. to about 150° C. for a time period of from about 1 hour to about 36 hours.

DESCRIPTION OF THE INVENTION

Figure 1:
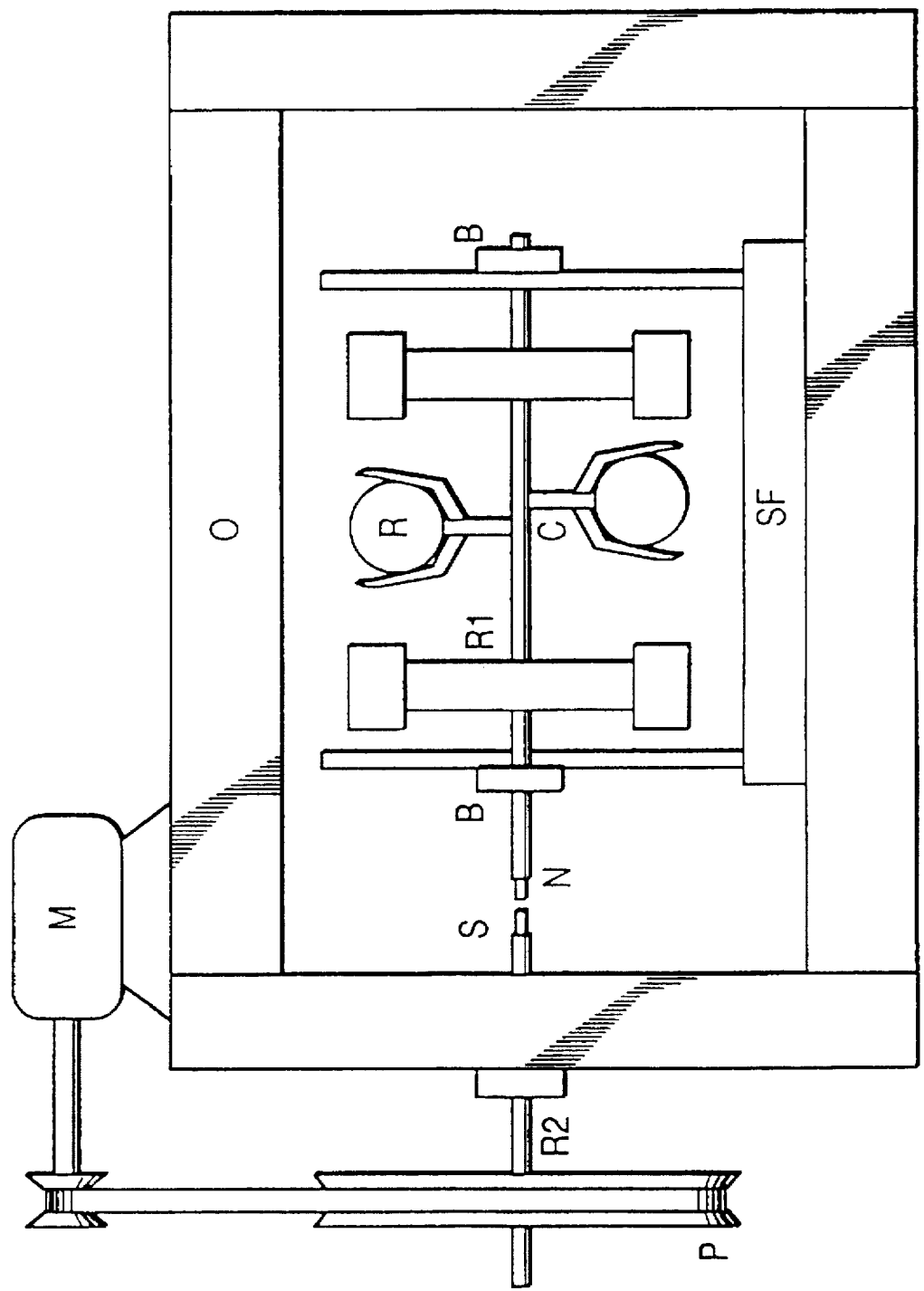
FIG. 1 is a schematic diagram of Reactor System 3.

This invention describes operating conditions that are significant improvement over the existing literature and do not require the removal of lignin from biomass. Previous researchers restricted their operating temperatures to ambient and below in order to create a very simple process without heaters. These simple processes required extremely long treatment times typically ranging from 8 to 150 days. Raising the treatment temperature will potentially decrease the treatment time, but runs the risk of degrading the lignocellulose. By systemically studying the process variable (lime loading, water loading, time, temperature) high temperature treatment conditions were identified that did not degrade the lignocellulose and resulted in treatment times that were orders of magnitude shorter. The economic impact is significant since the reactor can be orders of magnitude smaller. Because lignin is not significantly removed, resulting biomass quantities are increased.

The previous research in lime pretreatment used very low water loadings. Since their processes operated at room temperature, good heat transfer was not an issue. They could operate with very little water since the thermal insulating properties of air were not detrimental. However, when operating at a higher temperature, the process benefits by including about ten times more water since its high heat capacity and heat transfer coefficient insure a uniform temperature. Higher water loadings also provides a medium into which the lime can be uniformly dispersed. Most of the previous research in lime treatment used relatively low time loadings whereas, using the methods of the invention, higher loadings can be considered because a lime recovery process is incorporated into the invention.

The present invention comprises economical methods for the pretreatment of a biomass. Pretreatment comprises the addition of calcium hydroxide and water to a biomass to render the biomass susceptible to degradation. Calcium hydroxide is inexpensive and much cheaper than other alkalis. It is safe to handle and, unlike the sodium residue, the calcium residue is little or no problem for animal feed. In an artificial rumen, calcium hydroxide produces calcium acetate which is also safe and nontoxic. Calcium hydroxide ($Ca(OH)_2$) as the lignocellulose pretreatment agent is therefore very economical. Further, there was also no significant difference in digestibility between $Ca(OH)_2$ pretreated material and $NH_3$ or NaOH pretreated material in animals.

In one embodiment, the invention is directed to a method for pretreating a lignocellulose-containing biomass to render the biomass amenable to digestion and comprises providing a lignocellulose-containing biomass, adding calcium hydroxide and water to the biomass to form a mixture, and maintaining the mixture at an elevated temperature and for a period of time sufficient to render the biomass of the mixture amenable to digestion. Types of useful biomass include grass, wood, bagasse, straw, paper, plant material, and combinations thereof. The amount of lignin in these types of biomass range between about 1% to about 40%. Lignocellulose-containing biomass to which the process of the invention is directed is preferably biomass containing less than about 30% lignin, more preferable biomass containing less than about 20% lignin, and more preferable biomass containing about 10% lignin such as grasses and non-woody plants.

Preferably, biomass to be pretreated is fed into a chipper, grinder, chopper, shredder or the like, to be reduced in size. Resulting biomass chips or particles are preferable about one-half inch or smaller. The biomass particles are then combined with calcium hydroxide and water to form an alkaline biomass mixture. The mixture contains between about 6 to about 19 grams of water per gram of dry biomass and preferably about 16 grams of water per gram of dry biomass. The mixture also contains between about 2 to about 50 grams of calcium hydroxide per 100 grams of dry biomass and preferably contains about 30 grams of calcium hydroxide per 100 grams of dry biomass. Depending on the type of biomass, the preferable amount may be more or less. Calcium hydroxide may be added before or after the water or as an aqueous solution or dispersion.

The aqueous calcium hydroxide/biomass mixture is maintained in reaction chambers, which are preferably stainless steel, at between about 40° C. to about 150° C., preferably between about 100° C. to about 140° C., and more preferably at about 120° C. Depending on the type of biomass, the temperature range may be between about 70° C. to about 110° C., between about 110° C. to about 150° C., or between about 50° C. to about 65° C. The temperature is maintained for between about 1 to about 36, preferably between about 1 to about 20 hours, more preferably about 3 hours. Again, depending on the type of biomass, the time period may be longer or shorter such as between about 15 to about 25 hours.

The resulting biomass has not been significantly reduced in quantity using this method, a large improvement in comparison to currently available treatments. In particular, lignin content is not significantly reduced. Preferably, lignin content is reduced less than about 30%, more preferably less than about 20%, and even more preferably only about 15%. A feature of this method is that pretreatment removes acetyl groups from hemicellulose which greatly increases digestibility without resulting in the removal of lignin molecules.

The pretreated biomass is digested by hydrolysis such as acid hydrolysis, enzymatic action, fermentation, or a combination of digestion methods. The digested biomass comprises material which are useful products such as alcohols, acids such as organic acids, sugars, ketones, starches, fatty acids, or combinations thereof. These products can be made into feedstocks such as chemical feedstocks, fuels, and other useful products. Due to the relatively gentle pretreatment conditions, the useful products are obtained in higher quantities and are of a higher quality than products obtained after other pretreatment methods. The maximum amount of material is converted into useful product with as little waste as possible. Further, no toxins or harmful chemicals are introduced into the biomass therefore none need to be removed or even tested for in the final product.

Another embodiment of the invention is directed to a method for recovering calcium from a biomass pretreatment process comprising pretreating the biomass with calcium hydroxide and water to form a mixture, and maintaining the mixture at an elevated temperature and for a period of time sufficient to render the biomass of the mixture amenable to digestion, carbonating the mixture or the liquid portion thereof to precipitate calcium carbonate, and recovering the precipitated calcium carbonate. The pH of the carbonated mixture is between about 8.5 and about 10.5, and preferably between about 9.0 and about 10. The calcium carbonate is precipitated in the mixture and can be recovered by filtration, hydroclone separation, sedimentation, centrifugation, or by combinations of these methods. The calcium carbonate may also be heated and converted into carbon dioxide and calcium oxide, and the calcium recovered as calcium oxide.

Alternatively, the pretreated mixture is treated with a carbonating agent, which is preferably carbon dioxide gas which is bubbled into the mixture, forming calcium carbonate. The pretreated and carbonated biomass is digested and the useful product separated from the remaining mixture or residual mixture. The residual mixture, comprising lignin and calcium carbonate, is heated, for example in a kiln, preferably a lime kiln, to convert the calcium carbonate into calcium hydroxide. The heat supplied to the kiln may be derived from the burning of the lignin, making for a highly economical overall process.

The following examples are offered to illustrate embodiments of the invention, but should not be viewed as limiting the scope of the invention.

EXAMPLES

Sample Preparation

Raw bagasse was collected from the Animal Science Department of Texas A&M University. For three years, it was lying in the open, covered only by a plastic sheet. Thus, it was first thoroughly washed with water and then dried in an oven (at 80° C.) for about 8 hours. Also, because bagasse deteriorates with storage time, the bagasse used in the present study was more recalcitrant than that used by Holtzapple et al., Appl. Biochem. Biotech. 28/29,59 (1991). The wheat straw was already clean and did not require washing. Softwood newspaper was the Bryan/College Station, Tex., Eagle newspaper. It was first shredded in a paper shredder. All materials were ground by a Wiley mill to 1×1 mm particle size and then passed through a 40 mesh sieve. Dry weight analysis was done by placing a small sample in an oven, at 80° C. for 24 hr and measuring the weight loss due to water evaporation.

Calcium Hydroxide Pretreatment

Calcium hydroxide pretreatment involves reacting biomass with calcium hydroxide in the presence of water at a relatively high temperature. The effectiveness of the pretreatment process was studied for several different reaction conditions. Process variables studied were lime loading (2 to 30 g Ca(OH)$_2$/100 g dry biomass), water loading (6 to 19 g water/g dry biomass), treatment temperature (50° C. to 145° C.) and treatment time (1 hour to 36 hours). The following three types of reactor systems were employed.

Reactor System 1: For initial pretreatment experiments, 500-ml glass Edenmeyer flasks were used as reactors. The flasks were sealed with rubber stoppers and placed in a 100-rpm shaking water-bath. This method was limited to 65° C., the highest temperature attainable by the water bath.

Reactor System 2: Erlenmeyer flasks were placed in an oven, with periodic manual shaking. Only one experiment, at 65° C., was performed by this method. This method resulted in lower yields, thus demonstrating that continuous shaking was required for effective mass transfer. Reactor System 3: Steel reactors were used for experiments in the 65° C. and 145° C. temperature range. To resist the corrosive nature of calcium hydroxide solutions, the reactors were constructed of 304 stainless steel. The reactors were, 1.5"I.D.×5" long, cylindrical nipples, with end caps on both ends. To provide mixing inside the reactors, a rotating device was fabricated in the Texas A & M Chemical Engineering Department's machine shop. A schematic diagram of this reactor system is shown in FIG. 1. This device holds the reactors (R) inside the oven (O) and, by rotating them continuously, provides tumble mixing of the contents. It has a steel rod (R1) supported from both ends on two ball bearings (B). The bearings are bolted on a steel frame (SF) that can be placed inside the oven. Six holes are drilled through this rod to hold the clamps (C) that hold the reactors. Set screws hold the clamps in place during rotation. Through the back side of the oven, a 1" hole is drilled. A small rod (R2) supported by a ball bearing (bolted on the oven wall) passes through this hole. A pulley (P) is mounted on the end that is outside the oven. A variable speed AC/DC motor (M) mounted on the top of the oven rotates R2. The steel rod that holds the reactors (R1) has a splined end (a small nut (N)) that couples with the pulley (via a socket (S)). This coupling arrangement allows the reactors to be placed in, and removed from, the oven with ease.

To perform the pretreatment experiments, the reactors were prepared by winding at least four layers of Teflon tape on both ends. One end was closed by placing the nipple in a vice and tightening the end cap by a pipe wrench. The reaction mixture was prepared by placing the measured quantities of biomass (7.5 g dry weight) and $Ca(OH)_2$ (according the lime loading) inside the reactors. The material was thoroughly mixed inside the reactors using a spatula. Measured amounts of water were then added to this dry mixed sample. The end cap was placed on the other end of the nipple and tightened. The reactors were then placed in boiling water for 5 to 15 minutes (depending on the pretreatment temperature) to pre-warm them. Prewarming the reactors is necessary to rapidly bring them to higher temperatures. They were then clamped and fixed on the rotating device and placed in the oven maintained at the desired pretreatment temperature. The motor was turned on and the system was left for the desired pretreatment time. After the treatment time elapsed, the reactors were removed from the oven and transferred to a water bath to rapidly lower the temperature to ambient temperature. Samples were then removed from the reactors for hydrolysis. A complete step-by-step procedure is given below.

Calcium Hydroxide Pretreatment—Reactor System 3

1. Remove the old Teflon tape and clean the threads at both ends. Wrap (clockwise) at least four layers of fresh Teflon tape.
2. Label and number all the reactors. 2 or 4 or 6 reactors can be run each time.
3. Close the reactors by placing the cap on one end. Hold the nipple in the vice and tighten the cap using a pipe wrench.
4. Weigh ground and sieved material that has 7.5 g dry weight. Using a funnel, pour it in the labeled reactors.
5. Weigh calcium hydroxide, according to the desired lime loading, and pour into the reactors with the biomass.
6. Using a spatula, mix $Ca(OH)_2$ and biomass thoroughly. This dry mixing is essential to ensure a uniform reaction.
7. Pour water according to desired water loading.
8. Close the ends of the reactors.
9. Place the reactors in boiling water for about 5 minutes, for a 50° C. run, to about 15 minutes, for a 135° C. run. The water boiler takes about 30 minutes to heat up, so it must be turned on before hand.
10. Heat the oven to the desired pretreatment temperature. The oven takes about 1 hour to reach a stable temperature. Keep the rotating device inside the oven during heating so that it gets prewarmed.
11. Clamp the reactors, making sure that the clamps are in the center of the reactors so that there is no blocking during rotation.
12. Place the clamps in the slots of the rotating rod and tighten the set screws.
13. Place the device in the oven and couple it with the motor using the coupling arrangement.
14. Turn on the motor and keep the rotation speed at the minimum possible. Make sure that the motor does not stall.
15. Observe the temperature of the oven.
16. After the pretreatment time has elapsed, take out the reactors and place them in a cold tap water bath. Let them cool for about 10 min.
17. Perform enzymatic hydrolysis.

Filter Paper Assay

The filter paper assay is commonly used to quantitatively study cellulose hydrolysis and measure cellulose activity. Filter paper is used since it is a readily available and reproducible substrate and is neither too susceptible nor too resistant to cellulase enzymes. The filter paper is incubated with various amounts of cellulase enzyme for 1 hour at 50° C. and pH of 4.8. The amount of reducing sugars released in 1 hour is measured by the Dinitrosalicylic Acid (DNS) assay. (Also see below). The amount of enzyme that produces 2 mg is equal to sugar (expressed as glucose) in 1 hour is equal to 0.185 International Units (1 IU=1 mmole glucose/min).

Figure 2:
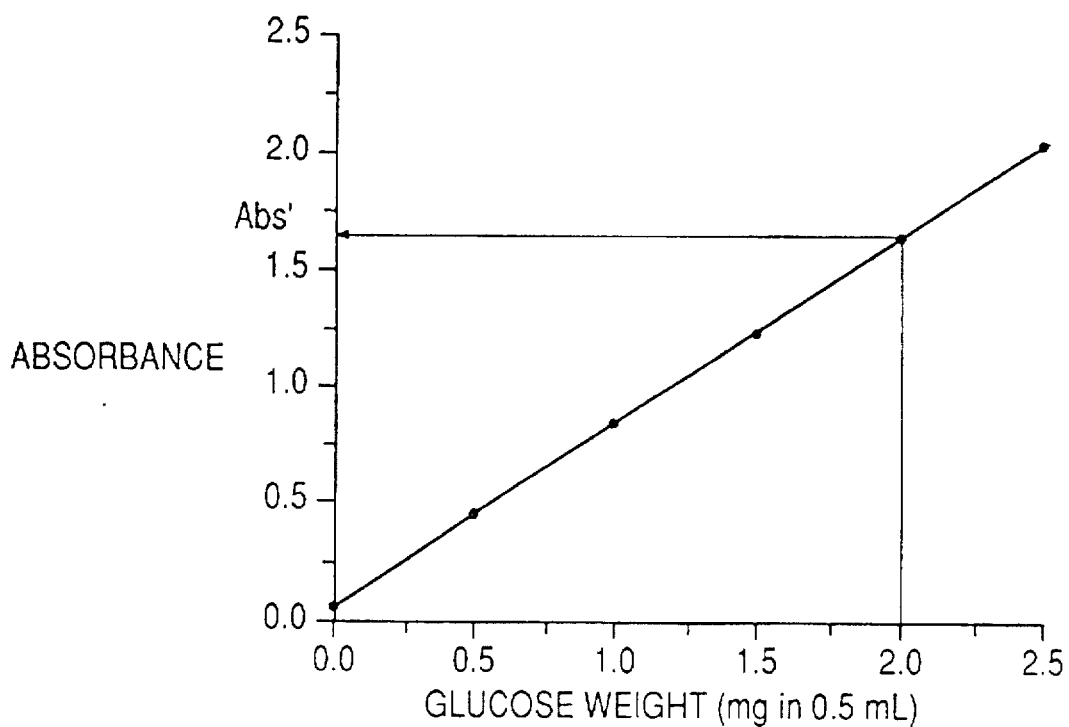
FIG. 2 is a glucose calibration curve for the filter paper assay.

Calibrate DNS reagent using glucose (along with filter paper):

1. Using a 500 mg/dl (5 mg/ml) glucose standard, prepare 0.5 ml samples in pairs of test tubes according to Table 5.
2. Add 1.0 ml of pH 4.8, 0.05M citrate buffer.
3. Add 1×6 cm filter paper strip (Whatmann #1, rolled in a curl). Vortex.
4. Incubate at 50° C. for 1 hour (use capped test tubes). Prevent any shaking.
5. Add 3.0 ml of DNS to each test tube.
6. Boil samples for 15 minutes in water bath.
7. Add 10 ml water and vortex.
8. Filter through 0.45 μm nylon membrane filter.
9. Measure the absorbance at 550 nm and prepare a calibration curve of absorbance vs. glucose concentration as shown in FIG. 2.

TABLE 5

| Prepare standard solutions for glucose calibration (for filter Paper Assay). | | | |
|---|---|---|---|
| Glucose Conc. (mg/ml) | Glucose Weight (mg) | Standard (ml) | Distilled Water (ml) |
| 1.0 | 0.5 | 0.10 | 0.40 |
| 2.0 | 1.0 | 0.20 | 0.30 |
| 3.0 | 1.5 | 0.30 | 0.20 |
| 4.0 | 2.0 | 0.40 | 0.10 |
| 5.0 | 2.5 | 0.50 | 0.00 |

Measure enzyme activity:

1. Add 0, 5, 10, 15, 20 mg enzyme to 10 ml, 0.05M citrate buffer, pH 4.8, and vortex.

2. Pipet 0.5 ml of prepared enzyme samples into pairs of test tubes.
3. Repeat steps 2 to 8 performed during calibration curve preparation.
4. Measure the absorbance at 550 nm.

Measure sugars in the enzyme:

1. Pipet 0.5 ml of 20 mg/ml enzyme sample into pairs of test tubes A.
2. Pipet 0.5 ml of distilled water into pairs of test tubes B.
3. Add 1.0 ml of pH 4.8, 0.05M citrate buffer to test tubes A and B.
4. Repeat steps 5 to 7 performed during calibration curve preparation.
5. Measure absorbance at 550 nm.
6. Calculate absorbance correction factor (ACF) as follows.

$$ACF = \frac{(Abs\ A - Abs\ B)}{(20\ mg\ enzyme/10\ ml) \times 0.5\ ml}$$

Calculate specific enzyme activity

1. Using the glucose calibration curve, calculate absorbance, the absorbance for 2 mg glucose weight (see FIG. 2).
2. Apply absorbance correction factor (ACF) to absorbance data from the enzyme results.

$Abs_{cor} = Abs - ACF \times E$ (where E=mg enzyme in 0.5 ml)

Figure 3:
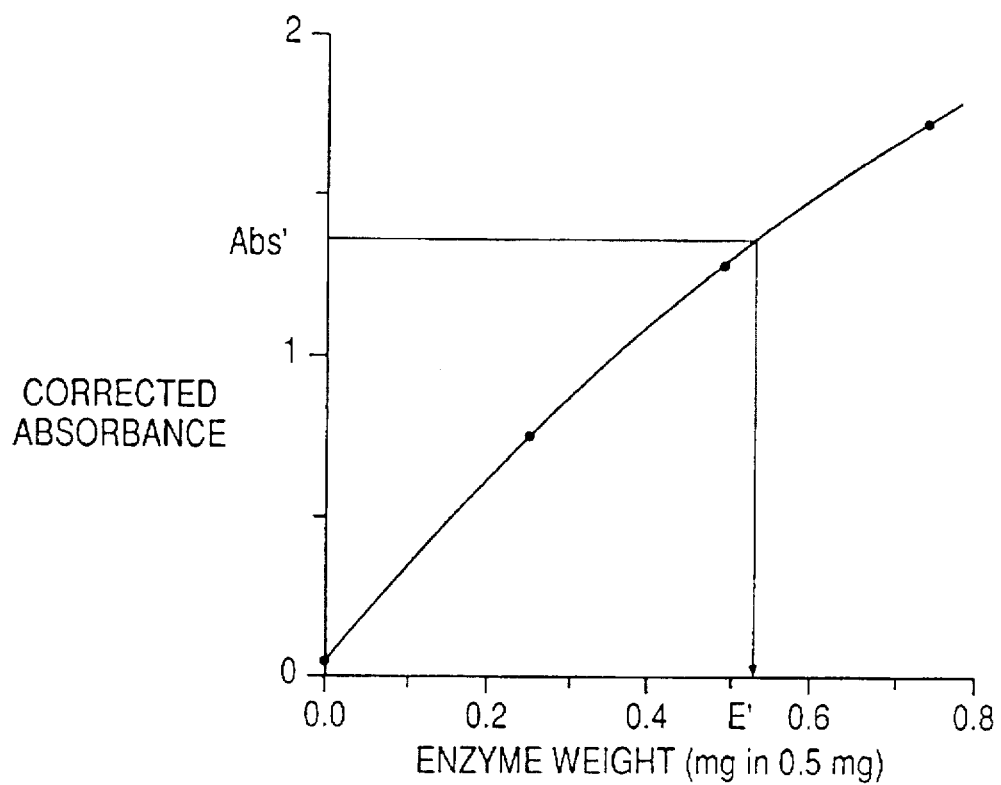
FIG. 3 is an enzyme calibration curve for the filter paper assay.

3. Plot $Abs_{cor}$ vs. E to get FIG. 3.

4. Find E' corresponding to Abs' using FIG. 3.
5. Calculate specific activity:

$$\text{Activity (IU/mg)} = \frac{2\ mg\ glucose}{E'\ mg\ h} \times \frac{1\ hour}{60\ min} \times \frac{mmole}{0.18\ mg\ glucose}$$

Material Balances

Material balances were performed to determine how much biomass was solubilized by pretreatment. Solubles were removed from pretreated and untreated bagasse by repeated washings with distilled water until the decanted water became colorless. Biomass was dried in ovens at 105° C. for 8 hours and placed in a desiccator to cool to room temperature. Twenty grams of the dried biomass was transferred into a centrifuge bottle and stirred with 500 ml water for 15 minutes. Bottles were centrifuged for 5 minutes at 3300 rpm and the water decanted by vacuum filtration. These steps were repeated until the filtrate was clear. Filtered cakes of biomass were dried in ovens at 105° C. for 8 hours and weighed. Results are shown in Tables 6 and 7. These data show that lime pretreatment does not remove much biomass. Only 3.65% of total weight was removed by pretreatment.

TABLE 6

Material Balance Between Raw and Washed Bagasse

| Components | Raw Sample | | Washed Sample | | Loss | |
|---|---|---|---|---|---|---|
| | Weight[a] (g) | Weight Percentage | Weight[a] (g) | Weight Percentage | Weight[a] (g) | Weight Percentage[b] |
| Total | 17.0224 | 100.00% | 16.5522 | 100.00% | 0.4702 | 2.76% |
| Ash | 0.7677 | 4.51% | 0.5479 | 3.31% | 0.2198 | 28.63% |
| Lignin | 3.7279 | 21.90% | 3.5455 | 21.42% | 0.1824 | 4.89% |
| Glucan | 7.4047 | 43.50% | 7.2416 | 43.75% | 0.1632 | 2.20% |
| Crude Protein | 0.2962 | 1.74% | 0.2235 | 1.35% | 0.0727 | 24.54% |
| Others[c] | 4.8275 | 28.36% | 4.9937 | 30.17% | −0.1662[d] | −3.44%[d] |

[a]105° C. dry weight
[b]Based on the initial weight of each component before washing.
[c]Including xylose and extractives.
[d]The negative sign indicates gaining weight on "other" components, which may be a random error.

TABLE 7

Material Balance Between Raw and Pretreated[a] & Washed Bagasse

| Components | Raw Sample | | Washed Sample | | Loss | |
|---|---|---|---|---|---|---|
| | Weight[a] (g) | Weight Percentage | Weight[a] (g) | Weight Percentage | Weight[a] (g) | Weight Percentage[b] |
| Total | 20.0964 | 100.00% | 18.8089 | 100.00% | 1.2875 | 6.41% |
| Ash | 0.9063 | 4.51% | 0.7279 | 3.87% | 0.1784 | 19.69% |
| Lignin | 4.4011 | 21.90% | 3.5680 | 18.97% | 0.8331 | 18.93% |
| Glucan(YSI) | 8.7419 | 43.50% | 9.3066 | 49.98% | −0.5647[d] | −6.46% |
| Crude Protein | 0.3497 | 1.74% | 0.1824 | 0.97% | 0.1673 | 47.84% |
| Others | 5.6974 | 28.35% | 5.0240 | 26.71% | 0.6734 | 11.82% |

[a]Pretreatment conditions: Temperature = 120° C., Pretreatment time = 1 h, Lime Loading = 0.1 g/g dry biomass, Water loading = 10 g/g dry biomass, and Particle size ≦ 40 mesh
[b]105° C. dry weight.
[c]Based on the initial weight of each component before pretreatment and washing.
[d]The negative sign indicates gaining weight on glucan, which may be a random error.

Determination of Carbohydrates

Carbohydrates make up a major portion of biomass samples. These carbohydrates are polysaccharides constructed primarily of glucose, xylose, arabinose, galactose and mannose monomeric subunits. Carbohydrate analysis was determined at both 45° C. and 105° C., basically as described by Grohmann et al. (Biotech. Bioeng. Symp. 14:139–57, 1984), wherein biomass samples were hydrolyzed to their monomer components and quantitated by ion mediated partition HPLC. Briefly, samples were milled through a 40 mesh screen using a Thomas-Wiley mill, if necessary to remove large chunks. Samples were dried in ovens at 45° C. or 105° C. Approximately 0.3 grams of the 45° C. sample was transferred to a glass test tube and stirred with 3.0 ml of 72% sulfuric acid until the sample was wetted with acid. The test tube was placed into a 30° C. water bath and incubated for 2 hours with periodic stirring to assure complete wetting. These steps were repeated using high purity sugar standards (glucose, xylose, arabinose, galactose, mannose) to correct for losses due to the destruction of sugars during the hydrolysis process. After incubation, samples were removed from the water bath and transferred to crimp top bottles using 84 ml of reverse osmosis deionized (RODI) water which resulted in a 4% acid solution. Bottles were stoppered, sealed with aluminum foil and autoclaved for one hour at 121° C. Autoclaved bottles were cooled and the solution neutralized with calcium carbonate to a pH of 6 or slightly higher. Neutralized solutions were vacuum filtered through grade 413 filter paper and the resulting filter cakes rinsed with RODI water. Filtrate volumes were recorded and the filtrate itself saved for HPLC analysis.

HPLC Analysis of Sugars

A portion of each filtrate from autoclaved samples from carbohydrate analysis was passed through a 0.45 micron filter into an autosampler vial and the vial sealed. Sugar standards at appropriate concentrations were expected to be in the range starting at the detection limit of the instrument and extending up to 4 mg/ml. An Aminex HPX-87C column was used for glucose, xylose and arabinose and an Aminex HPX-87P was used for mannose and galactose. Some samples were run on both columns.

A calibration curve for each sugar to be quantitated was made and from these curves, the concentration of sugars (mg/ml) present in each hydrolyzed solution was determined by HPLC and calculated as follows:

percent sugar recovered =

$$\frac{\text{conc. detected by } HPLC \text{ (mg/ml)}}{\text{known conc. of sugar before hydrolysis (mg/ml)}} \times 100$$

percent sugar recovered values were used to correct for sugar concentrartion values from HPLC for each of the hydrolyzed samples:

$$\text{corrected sugar conc.} = \frac{\text{sugar conc. obtained by } HPLC \text{ (mg/ml)}}{\% \text{ sugar recovered}/100}$$

Percentages of each sugar present in the hydrolyzed samples on a 105° C. dry weight basis was calculated as follows:

$$\frac{\text{percent}}{\text{sugar}} = \frac{\text{corrected sugar conc.} \times (1 \text{ g}/1000 \text{ mg}) \times \text{volume filtrate}}{\text{sample weight} \times (\text{total solids } 105° \text{ C.}/\text{total solids } 45° \text{ C.})}$$

Determination of Klason Lignin in Biomass

As before, biomass was passed through a 40 mesh screen to remove large chunks of biomass if needed. The pretreated biomass was dried at 105° C. One gram of dry biomass placed into a test tube along with 15 ml of chiller (15° C.) 72% $H_2SO_4$ and stirred for one minute or until thoroughly mixed. The mixture was left to stand for 2 hours at 20° C. and stirred every 15 minutes. Hydrolyzate was transferred to a flask and dilute to 3% acid with 560 ml of distilled water which was boiled gently for 4 hours under a reflux condenser. Reflux solution was vacuum filtered through a filtering crucible that had been ignited and achieved a constant weight of ±0.1% upon reheating and the volume of filtrate recorded. Ten to fifteen mls of filtrate was decanted and saved for acid-soluble lignin determination. The flask was washed with hot deionized water to remove any particles clinging to the flask's inner surface and the solution vacuum filtered free of acid. The crucible contents were dried at 105° C. for 2 hours until a constant weight was achieved upon reheating. The crucible was cooled in a desiccator and weighed. To correct for acid-insoluble ash, the crucible containing the dried residue was ashed at 575° C.±25° C., cooled in a desiccator and weighed. Lignin weight was determined as percent dry biomass as follows:

$$\% \text{ Klason lignin} = \frac{\text{wt. crucible plus acid-insoluble residue} - \text{crucible plus ash}}{\text{initial sample wt.}} \times 100$$

Results are shown in Tables 6, 7 and 8.

Determination of Acid-Insoluble Lignin in Biomass

Acid solubilized lignin was determined for the pretreatment method. Filtrate saved from determination of Klason lignin content was analyzed spectrophotometrically from absorbance at 205 nm using a 10 cm light path cuvette and a 3% solution of $H_2SO_4$ as a reference blank. Absorptivity (extinction coefficient) value of 110 L/g-cm was used to calculate the amount of acid-soluble lignin present in the filtrate. The percent acid-soluble lignin on a 105° C. dry weight basis was calculated as follows:

$$\% \text{ acid-soluble lignin, dry wt. basis} = \frac{(A/bxa) \times df \times V}{(1000 \text{ cc}/1 \text{ L}) \times W} \times 100$$

wherein A is the absorbance at 205 nm, df is the dilution factor, b is the cell path length of 1 cm, a is the absorptivity value of 110 L/g-cm, V is the filtrate volume, and W is the initial sample weight in grams. Results are shown in Tables 6, 7 and 8.

Determination of Ash in Biomass

Ash is defined as the residue remaining after ignition at 575° C.±25° C. for a period of time sufficient to burn off the carbon fraction. To determine ash content, a clean crucible was placed in a muffle furnace set at 575° C.±25° C. and ignited to constant weight (±0.1% change in the amount of moisture present upon one hour of reheating). The crucible was removed and placed in a desiccator to cool to room temperature and weighed. Between 1–3 grams of the 105° C. dried samples was placed in these crucibles which were again placed into the muffle furnace set at 575° C.±25° C. for at least three hours or longer if needed to burn off the carbon fraction. After ignition was complete, as indicated by the absence of black particles, the furnace was turned off and the door opened to allow the crucibles to cool. Samples were removed and placed in a desiccator to cool to room temperature. Each sample was weighed and the percent ash determined as follows:

% ash, dry wt. basis =

$$\frac{\text{wt. ash residue plus container} - \text{wt. ash dried container}}{\text{wt. 105° C. dried sample}} \times 100$$

Results are shown in Tables 6, 7 and 8.

TABLE 8

Comparison of Water-soluble Weight Percentages of Each Bagasse Component from Washing Only and Washing plus Lime Pretreatment

| | Loss Weight Percentage[a] | |
|---|---|---|
| Components | Wash Only | Wash plus Pretreatment |
| Total | 2.76% | 6.41% |
| Ash | 28.63% | 19.69% |
| Lignin | 4.89% | 18.93% |
| Glucan | 2.20% | −6.46%[b] |
| Crude Protein | 24.54% | 47.84% |
| Others | −3.44%[b] | 11.82% |

[a]Weight percentage based on the initial weight of each component.
[b]The negative sign indicates gaining weight on glucan and "other" components, respectively, which may be a random error.

Enzymatic Hydrolysis Procedure

The pretreated material (7.5 g dry weight) was transferred from the reactors to 500-ml Erlenmeyer glass flasks. The operating pH and temperature for the enzyme system were kept at 4.8 and 50° C. respectively. The pH was reduced from about 11.5 to 4.8 by adding acetic acid. The total liquid volume was increased to 150 ml by adding distilled water to obtain a 50 g/L slurry of biomass. The required amounts of cellulase and cellobiase we added to the mixture, and the flasks were stoppered and kept in a 100-rpm shaking air bath at 50° C. for 3 days. The enzymatic hydrolysis of control materials was performed using 150 ml of 0.05M, pH 4.8 citrate buffer.

After 3 days, 1 ml liquid samples were withdrawn from each flask using a 1000-ml Eppendorf pipet. The samples were boiled in capped test tubes for 30 minutes to denature the enzyme, thus avoiding further hydrolysis. The boiled samples were filtered through 0.45-μm nylon membrane filters. The reducing sugar concentration was measured using the DNS assay (Miller, G. L., Anal. Chem. 1959, 31, 462) with glucose as the calibration standard. Thus, the sugar yields are reported as equivalent glucose/g dry biomass. Both cellulase and cellobiase contain sugars. To measure these sugars, enzymes were added to 150 ml of water in the same concentration as used previously, but without any biomass. One ml samples were taken to measure the sugar concentration. This measured sugar in the enzyme amounts to a correction of 45 mg eq. glucose/g dry biomass that was subtracted from the 3-day reducing sugar yields from the pretreated biomass. The hydrolysis samples were diluted from 13 to 33 times to bring the concentration within the assay range (0.1–1.0 mg/ml).

A detailed hydrolysis procedure is given below:

1. Open one end of the reactors and empty the contents (as much as possible) into the labeled 500-ml Erlenmeyer flasks.
2. To completely transfer the biomass, use water to wash the reactors. Pour this water and biomass mixture into the flasks. Add enough water such that the total liquid volume (water added during the wash+water added during pretreatment) is 140 ml.
3. Add glacial acetic acid to the mixture until the pH reaches 4.8. During acetic acid addition, continuously monitor the pH and stir using a magnetic bar. Note the volume of acetic acid added. If the pH goes below 4.8, use $Ca(OH)_2$ to raise it to 4.8.
4. Add more water to bring the total liquid volume to 150 ml.
5. Add 0.259 g cellulase powder "Cytolase 300 P" (filter paper activity, 215 IU/g powder) and 0.652 ml cellobiase "Novozyme" (activity 250 CBU/ml). Cytolase 300 P was supplied by Genencor, Inc. (South San Francisco, Calif.) and cellobiase was supplied by Novo Laboratories (Wilton, Conn.). The cellulase loading was 7.4 IU/g dry pretreated lignocellulose and the cellobiase loading was 22 CBU/g dry lignocellulose.
6. Place the flasks inside the 100-rpm shaking air bath at 50° C.
7. Close flasks with rubber stoppers after the flasks have been warmed for 10 min.
8. Keep flasks in the bath for 3 days.
9. Withdraw 1 ml of sample a various time intervals (0 h, 1 h, 3 h, 6 h, 10 h, 16 h, 24 h, 36 h, 48 h, 72 hours) and boil them for 30 minutes in capped test tubes.
10. Filter samples through 0.45 μm nylon membrane filter. Perform DNS assay to measure reducing sugars as explained below.

Figure 4:
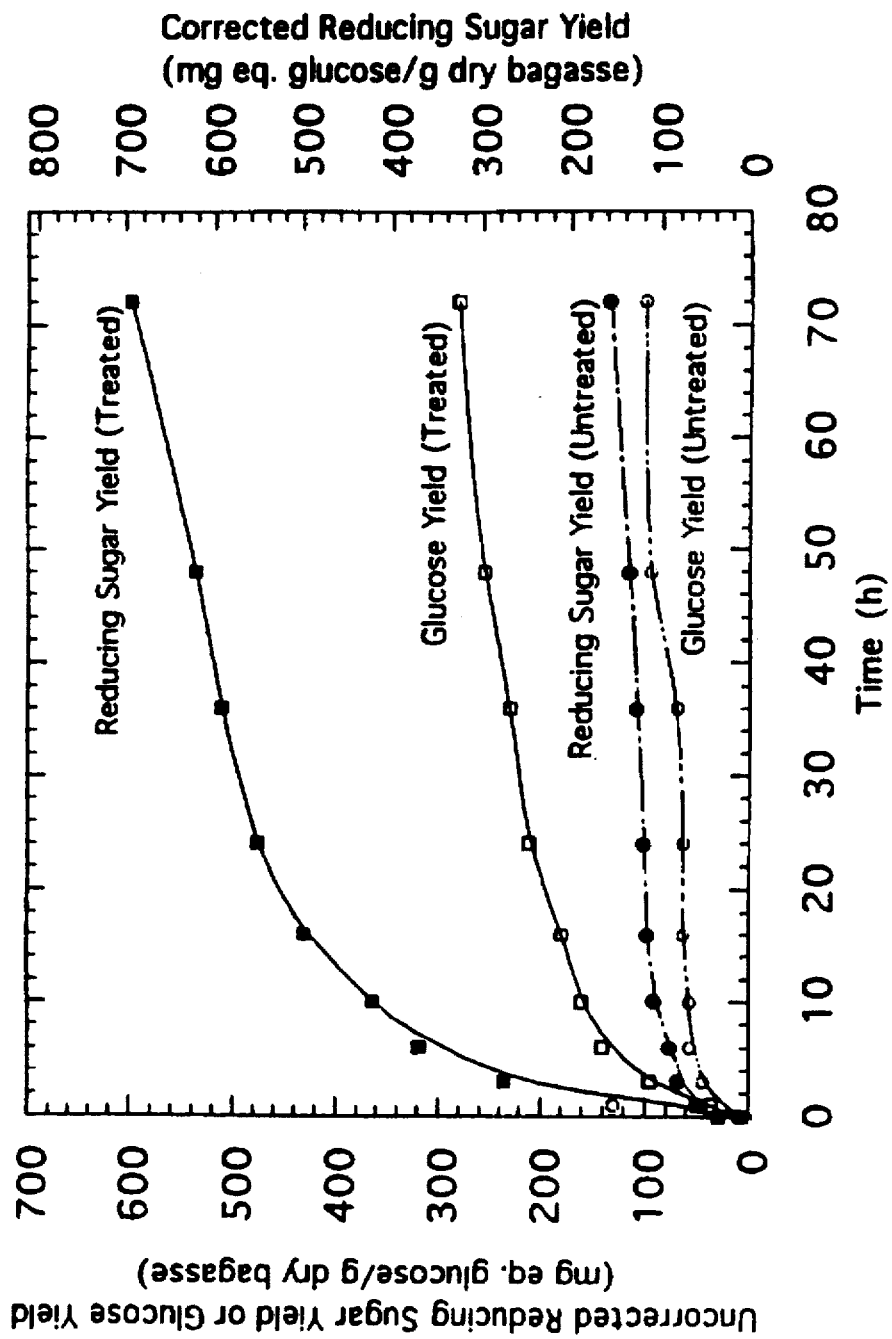
FIG. 4 is enzymatic hydrolysis profiles of bagasse.

An enzymatic hydrolysis profile of bagasse comparing glucose and reducing sugar yields in both pretreated and untreated samples in shown in FIG. 4.

Dinitrosalicylic Acid (DNS) Assay

The DNS assay is the most commonly used technique for measuring reducing sugars released by cellulose hydrolysis. A glucose standard is used for the calibration, thus the reducing sugars are measured as "equivalent glucose."

Prepare DNS reagent:

1. Dissolve 10.6 g of 3,5-dinitrosilicylic acid crystals and 19.8 g NaOH in 1416 ml of distilled water.
2. Add 306 g Na-K-tartrate (Rochelle salts).
3. Melt phenol crystals under a fume hood at 50° C. using a water bath. Add 7.6 ml of phenol to above mixture.
4. Add 8.3 g sodium meta-bisulfite.
5. Add NaOH, if required, to the solution obtained to adjust pH to 12.6.

Calibrate DNS reagent:

1. Using a 200 mg/dl (2 mg/ml) glucose standard, prepare 1 ml samples in pairs of test tubes according to Table 5.
2. Take 0.5 ml of each sample.
3. Dispense 1.5 ml of DNS reagent into each test tube using a 5-ml Brinckmann dispensette.
4. Place the caps on the tubes and vortex.
5. Boil samples in a water bath for 15 minutes.
6. Cool the test tubes for a few minutes. Add 8 ml of distilled water and vortex.
7. Zero the spectrophotometer at 550 nm with distilled water (Note: to stabilize the spectrophotometer it should be turned on for at least 1 hour before using).
8. Measure the absorbance.

Figure 5:
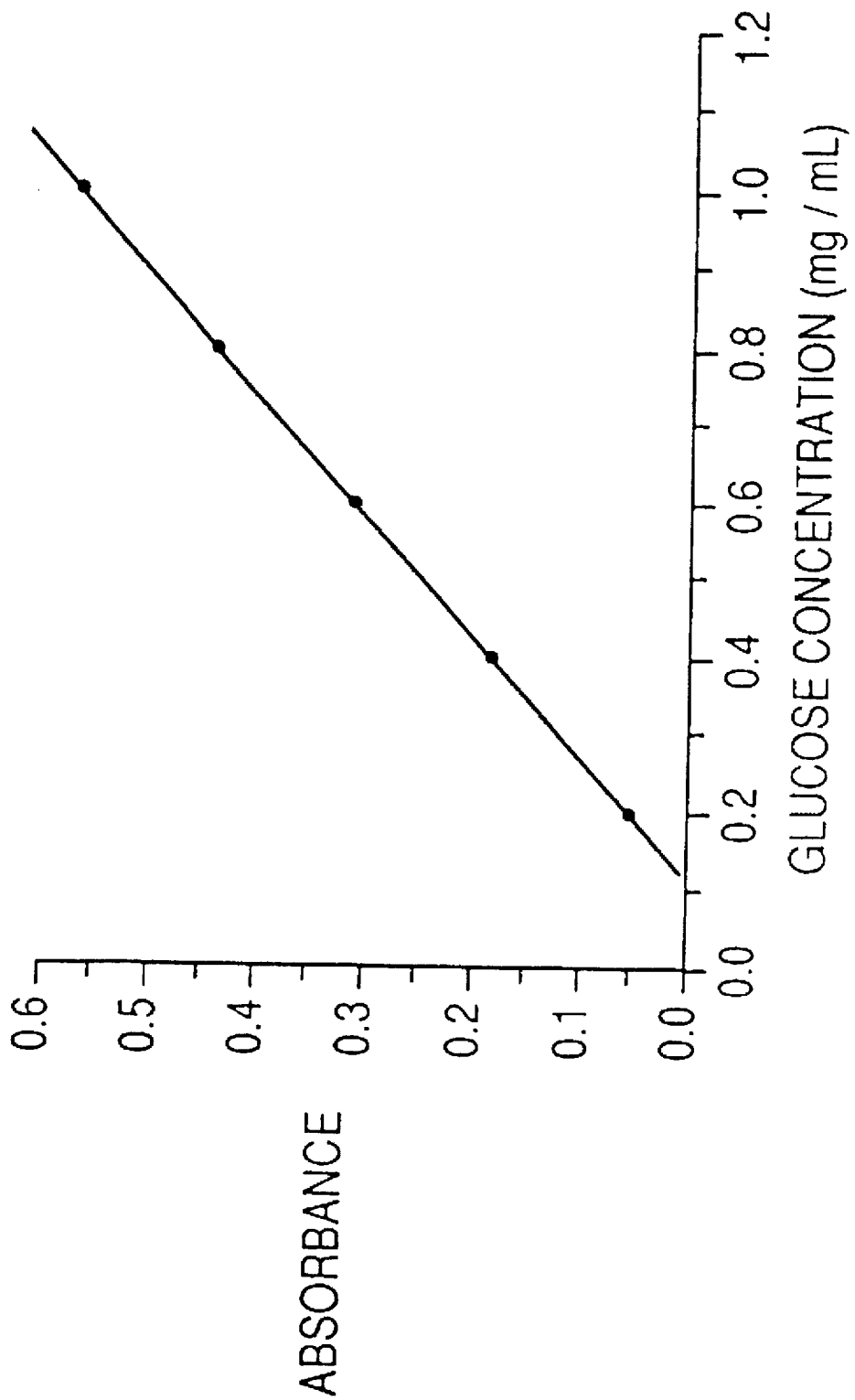
FIG. 5 is a calibration curve for the DNS assay.

9. Prepare a calibration curve as shown in FIG. 5.

TABLE 9

| Prepare standard solutions for glucose calibration (for DNS Assay.) | | |
|---|---|---|
| Glucose Concentration (mg/ml) | Standard (ml) | Distilled Water (ml) |
| 0.2 | 0.10 | 0.90 |
| 0.4 | 0.20 | 0.80 |
| 0.6 | 0.30 | 0.70 |
| 0.8 | 0.40 | 0.60 |
| 1.0 | 0.50 | 0.50 |

Measure reducing sugars of samples:
1. Dilute the filtered sample into a pair of test tubes such that the sugar concentration lies between 0.1 to 1.0 mg/ml.
2. Vortex the diluted sample.
3. Pipette 0.5 ml of each diluted sample.
4. Dispense 1.5 ml DNS reagent into each test tube.
5. Repeat steps 4 to 8 used in preparation of calibration curve.
6. Calculate sugar concentration from the absorbance of the samples using the calibration curve.
7. Calculate the reducing sugar yield by the following expression:

$$Y = S \times D \times 20$$

Y=reducing sugar yield (mg eq. glucose/g dry biomass)
S=sugar concentration in sample (mg eq. glucose/ml)
D=dilution factor
20=150 ml liquid volume/7.5 g dry biomass

NMR Measurement of Acetate Removal by Pretreatment

Figure 6A:
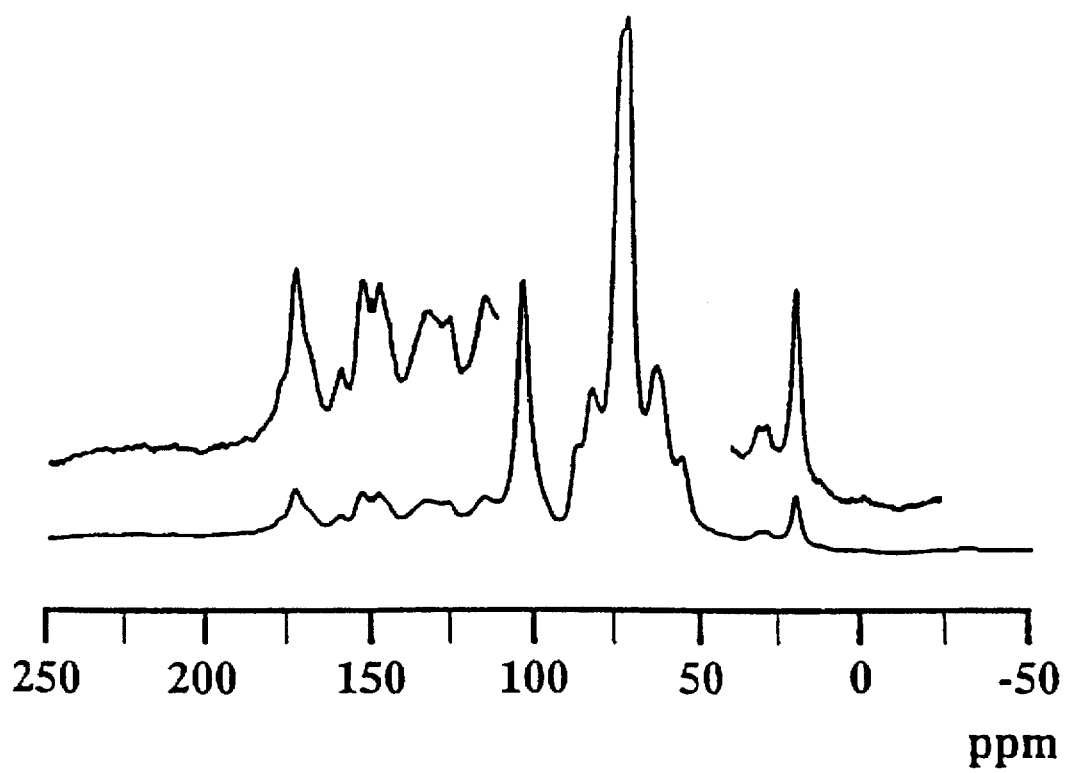
FIG. 6 is the NMR spectra for (a) untreated and (b) lime pretreated bagasse.
Figure 6B:
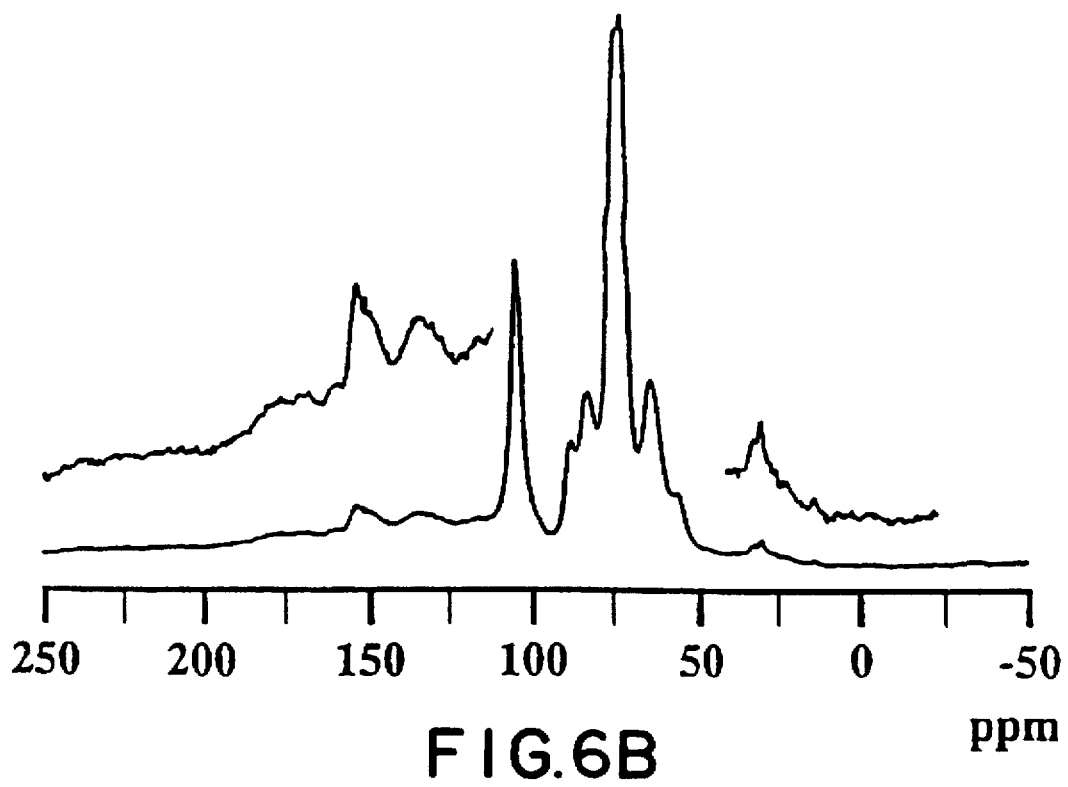

Solid-state $_{13}C$ nuclear magnetic resonance (NMR) with cross polarization and magic-angle spinning was used to measure chemical changes resulting from the lime pretreatment including breakage of ester linkages (e.g. xylan acetyl groups), benzene ring cleavage in lignin and biomass oxidation. FIG. 6 is the NMR spectra of raw bagasse and lime pretreated bagasse. The peak at 18 ppm corresponds to methyl groups and the peak at 175 ppm corresponds to carbonyl groups. Both peaks are essentially eliminated after lime pretreatment indicating that acetate (methyl plus carbonyl) is essentially removed which strongly increases biomass reactivity.

These results show that only about 14% of lignin is removed by the lime pretreatment procedure, while a satisfactory sugar yield was reached (598 mg eq. glucose/g dry bagasse for uncorrected sugar yield and 694 mg eq. glucose/g dry bagasse for corrected sugar yield). Substantial amounts of lignin remain in the bagasse. As only the acetate groups are removed, lignocellulose digestibility is increased.

Calcium Hydroxide Recovery

Two factors motivate recovery of calcium hydroxide from the pretreated biomass. First, an inexpensive recovery and recycle process will reduce the pretreatment costs. Second, high calcium residues have a detrimental effect on its use as cattle feed. Thus, reducing the calcium content results in a more utilizable material. The method for recovering $Ca(OH)_2$ is to wash the pretreated material with water, and to contact or react this wash water containing lime with carbon dioxide. This converts soluble $Ca(OH)_2$ to insoluble $CaCO_3$ that can be removed by precipitation. The $CaCO_3$ can then be heated to produce CaO and $CO_2$. The CaO is hydrated to $Ca(OH)_2$ which can be reused as the lignocellulose treatment agent. Carbon dioxide can, in turn, be reused for lime recovery. Thus, ideally, it is a system capable of total recycling.

The carbonate concentration is quite low when the pH is below 9.5. Thus, to form and precipitate more $CaCO_3$, the pH was maintained above 9.5.

All the recovery experiments were done using bagasse. The experiments to study the recovery process were conducted by two different approaches: Continuous Recovery and Batch Recovery.

Figure 7:
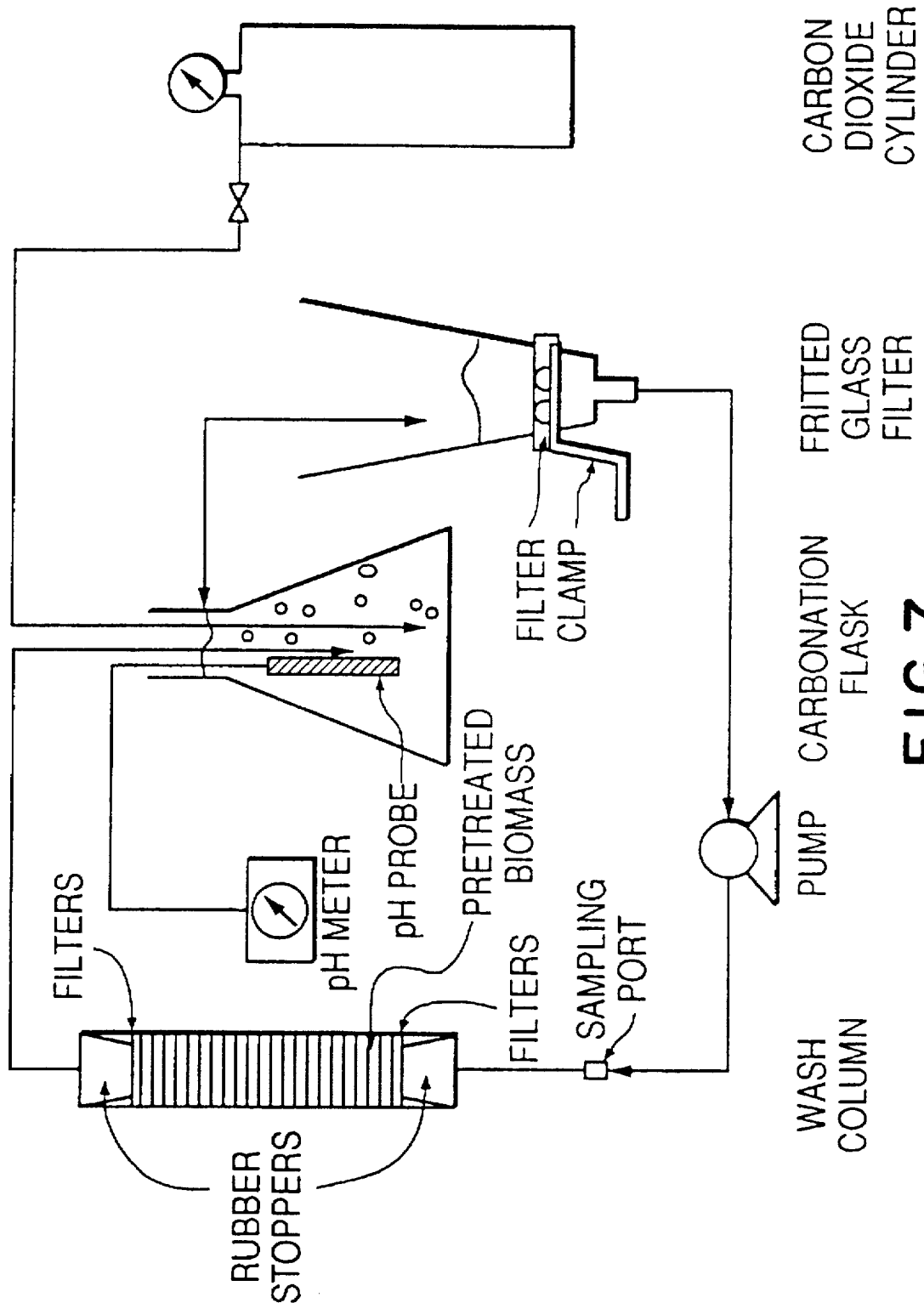
FIG. 7 is a flow diagram for continuous calcium hydroxide recovery.

1. Continuous Recovery: A systematic flow diagram of the continuous recovery experimental apparatus is shown in FIG. 7. The pretreated bagasse was packed in a 1" I.D.×8.5" high glass column. Rubber stoppers at both ends had connections for the inlet (bottom) and the outlet (top). Filters (nylon cloth) were glued on both stoppers. A peristaltic pump (Watson-Marlow, 502S) pumped water through the column. The average volumetric flow rate was 20 ml/min. The outlet from the column went to a 300-ml flask. Carbon dioxide was bubbled through the lime-saturated liquid in this flask to produce $CaCO_3$. A pH probe was placed in this flask to continuously monitor the pH. The pH was maintained near 9.5 by bubbling only as much $CO_2$ as was required to lower the pH from about 12.0 to 9.5. However, because good pH control was lacking, when the pH dropped below 9.5, the required amount of $NH_4OH$ (about 1 or 2 ml) was added to bring the pH back to 9.5. The overflow from the flask went to a filter assembly. Although most of the $CaCO_3$ remained in the flask, filtration was required to remove the $CaCO_3$ present in the overflow. A glass fiber filter (G6, Fisher Scientific, Inc.) was placed between the fritted glass filter and glass jar. A clamp was used to hold it and provide a good seal. The pump suction was the driving force for filtration. The filters were replaced periodically when they clogged with the $CaCO_3$ paste. The filtered water was then pumped back to the column for washing, thus completing the cycle.

The washing was stopped after about one hour. The wash water left in the glass jar clamped to the filter, was transferred to the flask and left for 24 hour to let $CaCO_3$ settle. Clear liquid (1 ml) was taken from the top of the flask. The clear liquid was decanted slowly and collected in another beaker. The bottom portion containing much higher amounts of $CaCO_3$ was discarded after measuring its volume. The same volume of fresh water was added to the system so that the liquid volume before and after precipitation and decantation remained the same. Further recovery of the lime remaining in the biomass was performed with this batch of decanted water for about 45 minutes. After the wash, the $CaCO_3$-saturated water was again left for precipitation and a sample of clear liquid was taken after this second precipitation.

To measure the calcium concentration in the water during washing, 1-ml samples were periodically taken from the column inlet and outlet. The calcium concentration was measured by the atomic absorption apparatus available in the Kinetics Group of the Texas A&M Chemical Engineering Department. Depending on the calcium concentration, the samples were diluted from 11° to 135° C. since the best yields were obtained between 65° C. and 100° C., this wide range ensured that the optimal temperature was found. The pretreatment times of 1 to 36 hours were logical choices since longer times were difficult to justify economically. Since mixing would ensure uniformity of the reaction mixture and probably result in a better pretreatment, continuous shaking was always employed except in one study that used periodic shaking.

In all the experiments, the 3-day reducing sugar yields were used as the measure of enzymatic susceptibility of lime-treated bagasse. The reducing sugar yields were calculated as mg equivalent glucose/g dry bagasse. Typically, 50% and 85% of the 3-day sugars were released in 6 hours and 24 hours, respectively. Table 10 summarizes the conditions and the reactor systems used in the various bagasse experiments.

TABLE 10

A summary of conditions used during various bagasse experiments.

| Exp. No. | Reactor System | Temp. (°C.) | Time (h) | Lime Loading (g Ca(OH)₂/100 g) | Water Loading (g water/g) | Particle Size |
|---|---|---|---|---|---|---|
| 1 | 1 | 65 | 1,3,6,12,24,26 | 30 | 10,15,19 | −40 mesh |
| 2 | 2 | 65 | 24 | 30 | 6,8,10,13,15,17,19 | −40 mesh |
| 3 | 3 | 65,125 | 12,6 | 30 | 6,8,10,13,15,17,19 | −40 mesh |
| 4 | 3 | 135 | 1,3,6,24 | 10,20,30 | 10,15 | −40 mesh |
| 5 | 3 | 100 | 1,3,24 | 10,20,30 | 10,15 | −40 mesh |
| 6 | 1 | 50 | 1,3,6,24 | 2,5,10,15,20,30 | 10 | −40 mesh |
| 7 | 3 | 85 | 3,24 | 5,10,15,20 | 10 | −40 mesh |
| 8 | 3 | 65 | 3,6,24 | 5,10,15,20 | 10 | −40 mesh |
| 9 | 3 | 65 | 24 | 10,15 | 10 | −1 × 1 mm +40 mesh |

The experiment at 50° C. (Bagasse Experiment, Example 2), lime loading=5 g Ca(OH)₂/100 g dry bagasse, water loading=10 g water/g dry bagasse, and treatment times of 1 and 24 hours was repeated thrice to find the error involved in measuring the 3-day reducing sugar yields. For the 1 hour run, the yields were 112, 125, 111 mg eq. glucose/g dry bagasse, showing a standard deviation of 7.8 mg eq. glucose/g dry bagasse. For the 24 hour run, the yields were 273, 256, 268 mg eq. glucose/g dry bagasse, showing a standard deviation of 8.7 mg eq. glucose/g dry bagasse. These standard deviations can be generalized to apply to the rest of the experiments, and thus other experiments were not repeated.

Calcium Acetate Inhibition Experiment

High calcium acetate concentrations are present in the hydrolysis mixture since acetic acid (about 5 ml glacial acetic acid for a sample treated with a lime loading of 30 g Ca(OH)₂/100 g dry bagasse) is used to neutralize the lime for pH adjustment. To measure the calcium acetate inhibition of enzymes, an experiment was performed in which group bagasse was ammoniated at the reported optimum conditions. These ammoniation conditions were: temperature=93° C.; treatment time=30 min., water loading=0.25 g water/g dry bagasse, ammonia loading=1.5 g NH₃/g dry bagasse, particle size=40 mesh.

Also, there was no explosion (as used in Ammonia Fiber Explosion process) since the pressure was slowly released. This pretreated material was hydrolyzed in enzyme solutions containing various calcium acetate concentrations. The calcium acetate solutions were prepared by adding various amounts of Ca(OH)₂ (according to the lime loadings used for the pretreatment) to 150 ml water, and then adding acetic acid to reduce the pH to 4.8. Thus, the calcium acetate concentration in these solutions was the same as for lime-pretreated materials. The enzymes were added to solutions only after the pH was brought to 4.8, thus there was no loss of enzyme activity due to high pH. The 3-day sugar yield obtained from this ammonia-treated material clearly shows that increased calcium hydroxide loadings decrease sugar yields due to calcium acetate inhibition of the enzyme. For the sample hydrolyzed without addition of Ca(OH)₂ to the saccharification flask, the sugar yield was 390 mg eq. glucose/g dry bagasse. This yield is 1.16, 1.14, 1.16, 1.15, 1.25 and 1.22 of that obtained from samples hydrolyzed in the solutions with 2, 5, 10, 15, 20 and 30 g Ca(OH)₂/100 g dry bagasse, respectively. In the subsequent experiments using lime pretreatments, these factors were used to correct the sugar yields. Since this approach is simplified and only approximately corrects for calcium acetate inhibition, the original data (without the correction factor) are reported in addition to the corrected data.

Overview of Data (Bagasse)

The 3-day reducing sugar yield for untreated bagasse sample (used as a control) was 40 mg eq. glucose/g dry bagasse which is only about 6% of the theoretical yield. Many different conditions as listed in Table 10 produced high sugar yields. Six high yielding conditions are tabulated in Table 8. The choice of conditions to be used industrially will depend not only on the sugar yields, but also on the expense associated with the conditions.

TABLE 11

Conditions resulting in high yields.

| Sample Number | Temp. (°C.) | Time (h) | Calcium Loading (g/100 g) | Water Loading (g/g) | Original Yield (mg/g) | Corrected Yield (mg/g) |
|---|---|---|---|---|---|---|
| 1 | 65 | 24 | 30 | 10 | 597 | 728 |
| 2 | 100 | 24 | 10 | 10 | 580 | 673 |
| 3 | 65 | 24 | 15 | 10 | 555 | 640 |
| 4 | 65 | 24 | 10 | 10 | 533 | 618 |
| 5 | 100 | 1 | 10 | 15 | 525 | 609 |
| 6 | 135 | 1 | 10 | 10 | 517 | 600 |

Softwood Newspaper Study

Softwood newspaper is the largest fraction of most residential municipal solid waste. Profitable utilization of softwood newspaper could help solve the evergrowing trash disposal problem. The composition of softwood newspaper is about 70% polysaccharides and 30% lignin, thus, the theoretical yield is bout 750 mg eq. glucose/g dry newspaper. The purpose of this study was to check the feasibility of using Ca(OH)₂ to pretreat newspaper. The conditions used for pretreating softwood newspaper are summarized in Table 12.

TABLE 12

Summary of conditions used during various newspaper experiments.

| Experiment Number | Reactor System | Temp. (°C.) | Time (h) | Lime Loading g Ca(OH)$_2$/100 g | Water Loading g water/g |
|---|---|---|---|---|---|
| 1 | 3 | 120 | 1,3,6,24 | 30 | 6,8,10,12,14,16 |
| 2 | 3 | 60 | 1,6,24 | 5,10,20,30 | 10 |
| 3 | 3 | 100,150 | 24,3 | 5,10,15,20,30 | 10,15 |

Overview of Data (Newspaper)

The 3-day reducing sugar yield from an untreated softwood newspaper sample, used as control, was 240 mg eq. glucose/g dry newspaper. Pretreatment processes that work well for many lignocellulosics do not work well for softwood newspaper. This probably results from its high lignin content. The yield improvements with Ca(OH)$_2$ pretreatment found in this present study are comparable to other pretreatments.

Of all the conditions tested, the best yield was obtained for 120° C., 24 hours, 30 g Ca(OH)$_2$/100 g dry newspaper and 16 g water/g dry newspaper. This yield was 344 mg eq. glucose/g dry newspaper (corrected: 430 rag/g). An interesting observation is that the pretreatment works better for either very severe conditions (120° C., 24 hours) or very mild conditions (65° C., 1 hour).

Wheat Straw Study

Wheat straw is one of the most abundant agricultural crop residues. In the United States, about 20% of cropland produces wheat, thus large quantities of wheat straw are generated. Typically, based on dry weight, wheat straw is 39% cellulose, 36% hemicellulose, and 10% lignin. According to this composition, the maximum theoretical yield is about 800 mg eq. glucose/g dry wheat straw.

The results for bagasse were used to guide the selection of treatment conditions. The lime loadings were 5, 10, 15 and 20 g Ca(OH)$_2$/100 g dry wheat straw. Only two water loadings were used. Treatment temperatures of 50, 65, 85 and 125° C., and treatment times of 1, 3 and 24 hours, were studied. A summary of the treatment conditions is tabulated in Table 13.

TABLE 13

Summary of conditions used during various wheat straw experiments.

| Experiment Number | Reactor System | Temp. (°C.) | Time (hours) | Lime Loading (g Ca(OH)$_2$/100 g) | Water Loading (gH$_2$O/g) |
|---|---|---|---|---|---|
| 1 | 3 | 65 | 3, 24 | 10 | 6, 10, 15, 19 |
| 2 | 3 | 65 | 1, 3 | 5, 10, 15, 20 | 10 |
| 3 | 1 | 50 | 3, 24 | 5, 10, 15, 20 | 10, 15 |
| 4 | 3 | 85 | 1, 3, 24 | 5, 10, 15, 20 | 10 |
| 5 | 3 | 125 | 1, 3, 12, 24 | 5, 10, 15, 20 | 10 |

Overview of Data (Wheat Straw)

As in the case of bagasse, several different conditions produced good yields. Since treatment time and temperature play the most important role in process economics, the selection of conditions will not depend strictly on sugar yields. Eight conditions that produced good yields are tabulated in Table 14.

TABLE 14

Conditions resulting in high yields from lime treated wheat straw.

| Sample Number | Temp. (°C.) | Time (hours) | Calcium Loading (g/100 g) | Water Loading (g/g) | Original Yield (mg/g) | Corrected Yield (mg/g) |
|---|---|---|---|---|---|---|
| 1 | 50 | 24 | 10 | 15 | 585 | 679 |
| 2 | 85 | 3 | 10 | 10 | 579 | 672 |
| 3 | 50 | 24 | 20 | 10 | 575 | 667 |
| 4 | 85 | 3 | 20 | 10 | 559 | 698 |
| 5 | 85 | 24 | 20 | 10 | 559 | 698 |
| 6 | 50 | 3 | 10 | 10 | 555 | 639 |
| 7 | 65 | 24 | 10 | 10 | 543 | 630 |
| 8 | 125 | 1 | 10 | 10 | 533 | 618 |

Calcium Recovery Study

The best yields for both bagasse and wheat straw were obtained for a lime loading of 10 to 20 g Ca(OH)$_2$/100 g dry material. Thus, an industrial process using such loadings would need significant amounts of lime. A process to recover and recycle lime can reduce the total of lime requirement. Since calcium hydroxide is quite cheap, one main requirement for a recovery process is that it should be simple and inexpensive.

A novel recovery process was developed in this invention. Ca(OH)$_2$ was leached or washed out of the pretreated biomass. The lime-saturated wash water was carbonated to convert Ca(OH)$_2$ to insoluble CaCO$_3$ that was subsequently settled. The recovered CaCO$_3$ can be calcinated to form CaO, which can be hydrated to Ca(OH)$_2$, and thus reused. In this study, the washing, carbonation and precipitation steps were performed. The experiments were conducted by two different approaches, namely, continuous and batch recovery processes.

Continuous Recovery Process

Three runs were performed to recover Ca(OH)$_2$ from bagasse by the continuous recovery method. The lime treatment conditions used in the continuous lime recovery study are tabulated in Table 15. The recovery results for the corresponding samples are tabulated in Table 13.

TABLE 15

Conditions used for treating bagasse for continuous recovery.

| Sample | Temp. (°C.) | Time (h) | Ca Loading (g/100 g) | Water Loading (g/g) |
|---|---|---|---|---|
| A | 85 | 3 | 10 | 10 |
| B | 85 | 3 | 15 | 10 |
| C | 100 | 1 | 10 | 10 |

TABLE 16

Change in calcium concentration during continuous recovery.

| Wash Water Sample | Calcium Conc. in Wash Water (ppm) Initial | (ppm) Final | Calcium Conc. in Bagasse (ppm) Initial | (ppm) Final |
|---|---|---|---|---|
| A | 1075 | 33 | 5.4 | 2.1 |
| B | 1392 | 10 | 8.1 | 2.3 |

TABLE 16-continued

Change in calcium concentration during continuous recovery.

| Calcium Conc. in Wash Water Sample | (ppm) Initial | (ppm) Final | Calcium Conc. in Bagasse (ppm) Initial | (ppm) Final |
|---|---|---|---|---|
| C | 947 | 19 | 5.4 | 2.0 |

The calcium content in the raw bagasse sample was 0.4 g Ca/100 g dry bagasse. The residual calcium content in the bagasse sample was brought down to about 2 g Ca/100 g dry bagasse from 5.4 g Ca/100 g dry bagasse (Samples A and C) and to 2.3 g Ca/100 g dry bagasse from 8.1 g Ca/100 g dry bagasse (Sample B). This shows that 68% of the added calcium was removed from Samples A and C and 75% of added calcium was removed from Sample B. The reduction in calcium content showed that the recovery process is working fairly well. However, if the pretreated lignocellulosics are to be used as cattle feed, this residual calcium concentration might be slightly high (1 to 2 g Ca/100 g dry biomass is desired).

One of the main drawbacks observed with the continuous recovery experiment was that there was some channeling inside the bagasse-filled column. Thus, the wash water was not contacting all of pretreated material. This definitely would lower the process effectiveness. With the use of some packing material and an efficient column design, it might be possible to increase the continuous recovery process efficiency. However, this invention used a second approach (i.e. batch recovery) that provides good contact by mixing the wash water and biomass.

Batch Recovery Process

In this experiment, instead of packing the pretreated material in a column, a glass beaker was used to mix the biomass with wash water. This wash water was saturated with $CaCO_3$ and had a pH of 8.7. The lime-saturated wash water obtained after filtration was contacted with $CO_2$ and the resulting $CaCO_3$-containing solution was allowed to settle. The pretreatment conditions and the corresponding calcium contents are given in Table 17 and Table 18, respectively.

TABLE 17

Conditions used for treating bagasse for batch recovery.

| Sample | Temp. (°C.) | Time (h) | Ca Loading (g/100 g) | Water Loading (g/g) |
|---|---|---|---|---|
| D, E | 65 | 24 | 10 | 10 |
| F, G, H, I, J, K | 65 | 24 | 15 | 10 |

TABLE 18

Change in calcium concentration during batch recovery.

| Sample | Number of Washings | (gNH$_4$OH/ 100 g) Wash Water | Calcium Conc. in Wash (ppm) Initial | (ppm) Final | Calcium Conc. in (g 100 g dry Bagasse) Initial | (ppm) Final |
|---|---|---|---|---|---|---|
| D | 6 | 0 | 955 | 7 | 5.4 | 1.7 |
| E | 6 | 0 | 892 | 16 | 5.4 | 1.7 |
| F | 6 | 0 | 1109 | 14 | 8.1 | 2.2 |
| G | 10 | 0 | 1192 | 13 | 8.1 | 1.5 |
| H | 10 | 0.2 | 1154 | 6 | 8.1 | 1.5 |
| I | 10 | 0.4 | 1056 | 6 | 8.1 | 1.4 |
| J | 10 | 1.6 | 1306 | 12 | 8.1 | 1.6 |
| K | 10 | 8.7 | 1070 | 4 | 8.1 | 1.7 |
| Untreated | 10 | 0 | 988 | 8 | 8.1 | 1.3 |

The first three samples (D, E, and F) used six washings whereas the other samples used ten washings. For a lime loading of 10 g $Ca(OH)_2$/100 g dry bagasse (Samples D and E), with six washings, the calcium concentration was reduced to about 1.7 g Ca/100 g dry bagasse, and for a lime loading of 15 g $Ca(OH)_2$/100 g dry bagasse (sample F) with six washings, the calcium concentration was reduced to about 2.2 g Ca/100 g dry bagasse. Thus about 75% of added calcium was removed.

Sample F and G received the same lime treatment. Whereas sample F was washed six times Sample G received four additional washings. These additional washings reduced the residual calcium content from 2.2 to 1.5 g Ca/100 g dry bagasse. Thus ten washings were able to remove 86% of the added calcium.

Since it is possible that the calcium atoms are chemically bound to the cellulose and other macromolecules of bagasse, simple washing with water may not work beyond a certain limit. To explore the possibility that bound calcium ions (+2), could be replaced by NH4+ions, the lime-treated bagasse was washed with an ammonium hydroxide solution. The ammonium hydroxide concentration varied from 0.2 to 8.7 g $NH_4$ OH/100 g water. The $NH_4OH$ was a 30% (w/w) solution of ammonia in water.

These experiments showed that the ammoniated wash water was not able to further recover calcium.

In all the previous samples, ammonia was added to the carbonated water to adjust the pH to 9.5. This ensured that the carbonate ions dominated, thus enhancing the precipitation of $CaCO_3$. For Samples H and I, samples for calcium analysis were drawn from settled wash water that was carbonated to pH 6.7, and also from settled carbonated wash water that has been raised to pH 9.5 by adding ammonia. It was found that it was essential to have the pH about 9.5 in order to effectively recover the $CaCO_3$. Although this experiment used ammonia to adjust the pH to 9.5, industrially this would be achieved by having a good control on the $CO_2$ addition. After lime treatment, the pH is about 11.5. Only the amount of $CO_2$ needed to reduce the pH to 9.5 would be added.

All the recovery experiments show that except for time loading, the other pretreatment conditions (i.e. treatment time, temperature and water loading) do not affect the recovery process. To determine if there are pretreatment reactions that hinder the recovery process, lime was recovered from untreated material, i.e. a physical mixture of bagasse and $Ca(OH)_2$. The calcium concentration in the wash water had a pattern similar to the other samples. The residual calcium content was 1.3 g Ca/100 g dry bagasse which is the lowest obtained from all the recovery experiments. Thus, there seems to be greater calcium binding to the biomass resulting from pretreatment process. However, the effect is small since ten washings of pretreated material had residuals of about 1.5 to 1.7 g Ca/100 g dry bagasse. Thus, there is not much difference in the recovery process for the pretreated material and for the untreated material.

An important question is how far can one atmosphere $CO_2$ lower the pH. *Trichoderma reesei* cellulase operates at pH 4.8. The pH of pretreated biomass is about 11.5, so an acid must be added to lower the pH. During alcohol fermentation processes, much $CO_2$ is generated, so it will be the cheapest acid for pH adjustment. To answer this question, a simple experiment was performed in which a few lime-saturated wash water samples were bubbled with 1 atmosphere $CO_2$ for about 15 minutes. The minimum pH that was reached was about 6.5. Thus a stronger acid than $CO_2$ will be required to lower the pH to 4.8. It would be more desirable to use a cellulase system that operates at pH 7 such as those in bacteria (e.g. *Clostridium thermocellum*).

Thus it is seen that calcium hydroxide is an excellent pretreatment agent. Many different conditions produced high sugar yields. There was no significant effect of water loading on sugar yields, although 10 g water/g dry material produced slightly higher yields. Lime loadings of 10 and 15 g Ca(OH)$_2$/100 g dry material worked well. It was generally found that the lower temperatures (50° C., 65° C.) required longer times (24 hours), whereas higher temperatures (135° C.) needed shorter times (1 hour) to produce high yields.

The recovery process was able to reduce the calcium content in biomass from 8.1 to about 1.5 g Ca/100 g dry material, thus recovering 86% of the added calcium.

Circulation Methods

Figure 8:
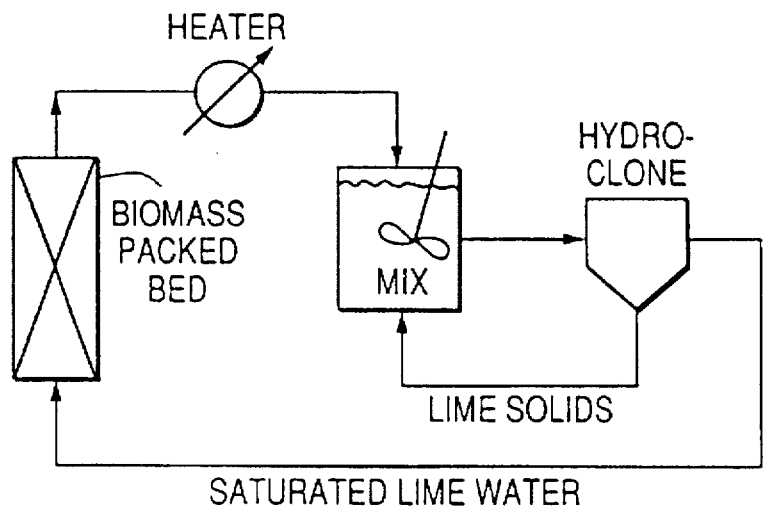
FIG. 8 is a schematic diagram of one embodiment of using a hydroclone to separate lime solids from lime solution.

To prevent the addition of excess lime, the biomass may be contacted with a solution of hot lime water. This may be accomplished in a number of ways:

Method 1: A solution of hot (temperature range of from about 40° C. to about 150° C.) saturated lime water is circulated through a packed bed of biomass for a time period of from about 1 hour to about 36 hours. As the solution exits the bed, it is heated to replace heat loss in the packed bed. The solution of saturated lime water can be prepared by mixing excess lime with water and separating the excess solid lime from the water phase by filtration, hydroclone separation (FIG. 8), settlement, or centrifugation.

Figure 9:
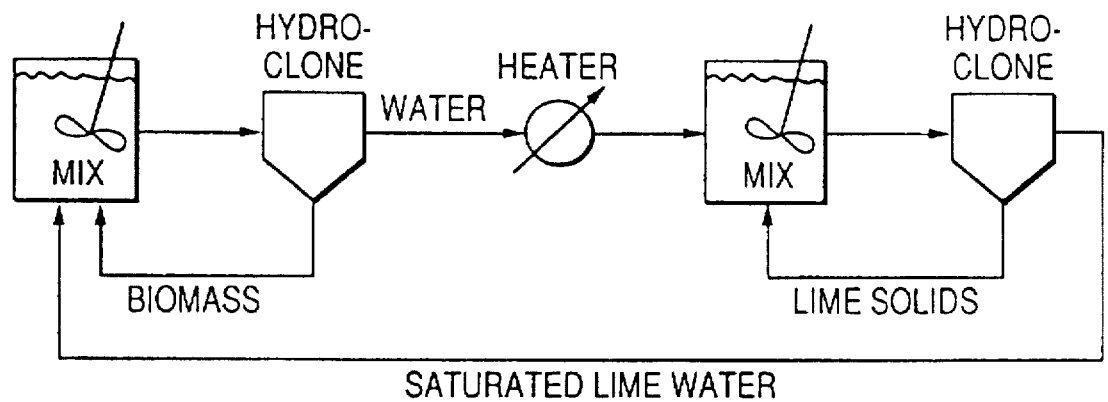
FIG. 9 is a schematic diagram of another embodiment of using a hydroclone to separate lime solids from lime solution.

Method 2: A solution of hot (temperature range of from about 40° C. to about 150° C.), saturated lime water is circulated through a stirred slurry of biomass for a time period of from about 1 hour to about 36 hours. The biomass is separated from the solution by a filter, hydroclone (FIG. 9), settler, or centrifuge. As the solution exits the hydroclone, it is heated to replace heat loss in the stirred slurry of biomass. The solution of saturated lime water can be prepared by mixing excess lime with water and separating the excess solid lime from the water phase by filtration, hydroclone separation (FIG. 9), settlement, or centrifugation.

In either Method 1 or Method 2, the lime solids must always be kept in contact with hot water at the highest temperature in the loop, such as between 40° C. and 150° C. This is required because lime is relatively more soluble in cold water than in hot water. If the water contacting the lime solids were cold, it would dissolve too much lime. Then, if the lime solution were heated later, lime would either precipitate out and foul the heat exchanger or deposit on the biomass. This explains why the water is heated before it contacts lime solids rather than after.

Different Permutations

Figure 10:
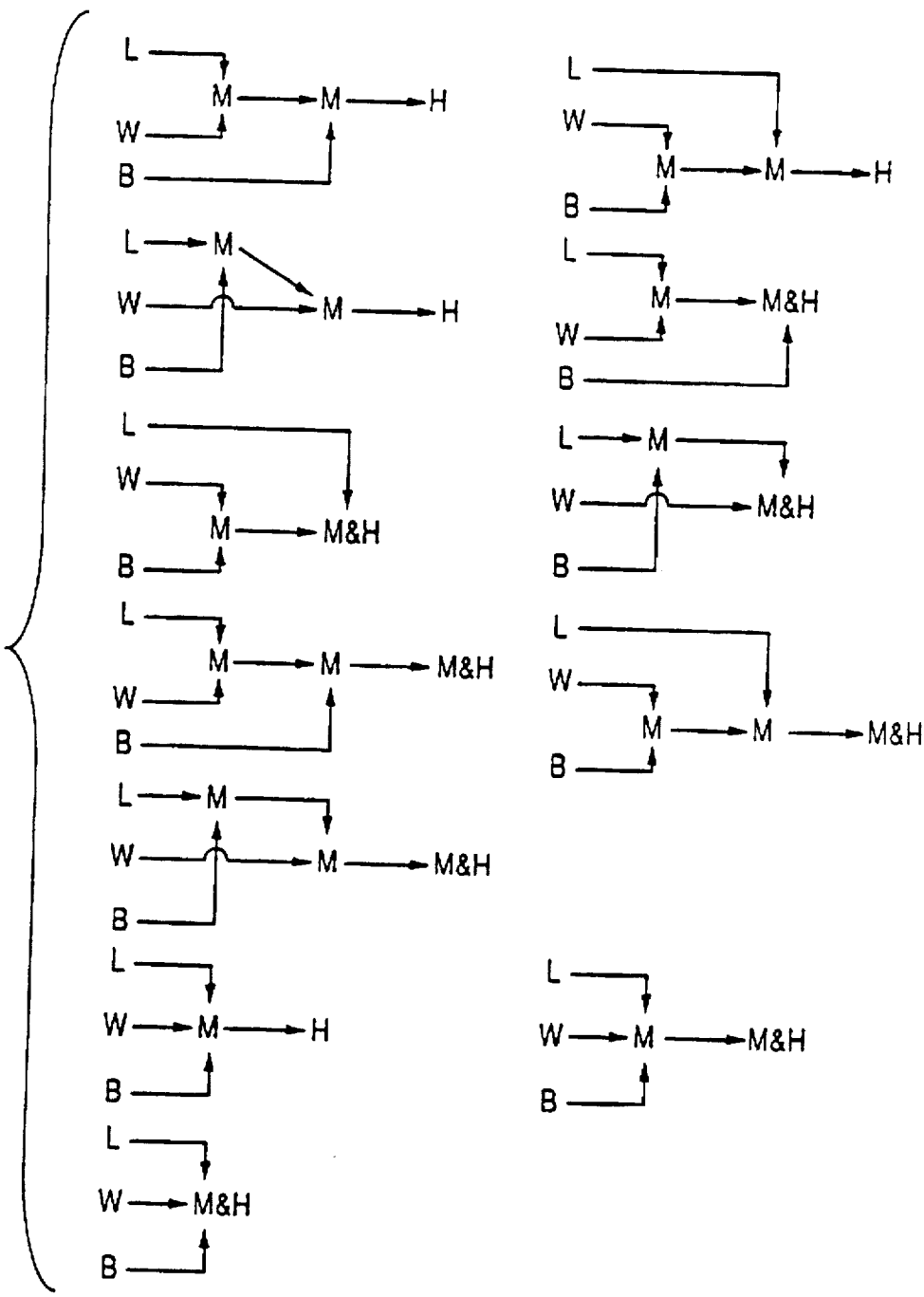
FIG. 10 is a schematic diagram showing different possible permutations of pretreating biomass with lime.

The materials needed for this invention include: Biomass, lime, or calcium hydroxide, and water. The manipulative procedures for this invention include: Mixing, heating, and simultaneous mixing and heating. Thus, these materials and procedures are capable of a number of permutations, as diagrammatically shown in FIG. 10. The notations used in FIG. 10 are: L=lime; W=water; B=biomass; M=mixing; H=heating; and M & H=simultaneous mixing and heating. An arrow in FIG. 10 signifies adding, introducing, or a step to be performed.

Lime Treatment Process for Ruminant Animal Feed Production

Figure 11:
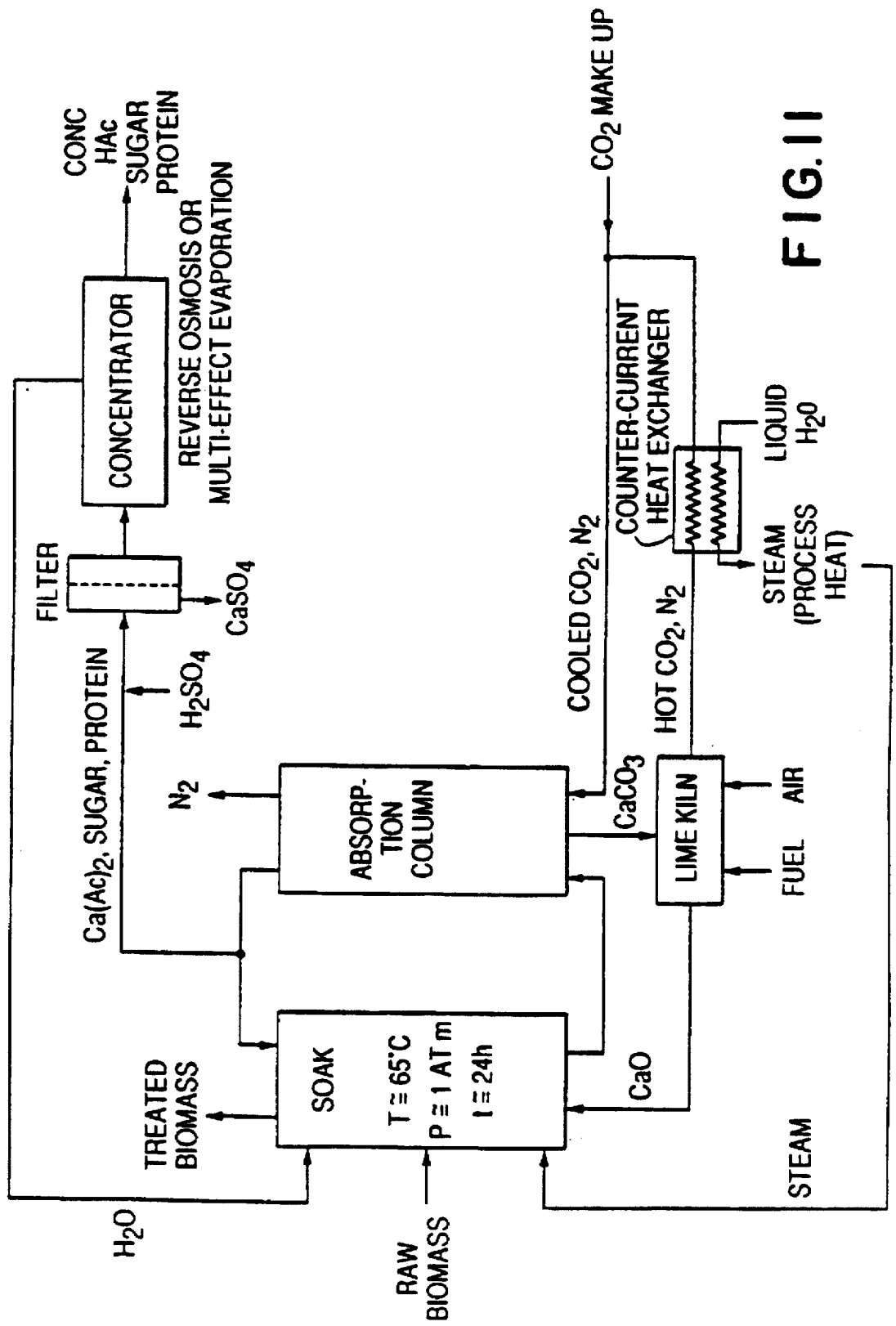
FIG. 11 shows the lime treatment process for ruminant animal feed production.

FIG. 11 shows the lime treatment process for ruminant animal feed production. The lime may be added directly to the biomass, as shown. Alternatively, the biomass may be contacted with a circulating solution of saturated lime water to avoid excess lime addition. Regardless of the addition method, the raw biomass is soaked in hot (ca. 65° C.) lime water for about 24 hours. Then, after the reaction is complete, the lime water is circulated through an adsorption column where it is contacted with carbon dioxide. The carbon dioxide reacts with the lime to form insoluble calcium carbonate which is filtered out and sent to a lime kiln. The calcium carbonate is heated to about 1200° C. in the lime kiln which drives off the carbon dioxide. The hot exit gases (primarily carbon dioxide with some nitrogen from the combustion air) are cooled in a countercurrent heat exchanger recovering high-pressure steam that may be used for electricity production and/or process heat. The cooled carbon dioxide is recycled to the absorption column where the carbon dioxide again reacts with lime water. Inerts, such as nitrogen, will exit the absorption column. Make-up carbon dioxide must be added to replace any losses.

The circulating lime water will contain free sugars and protein extracted from the biomass. In addition, there will be some calcium acetate produced from the acetyl groups on the hemicellulose. A bleed stream will be taken off from the circulating loop that will be acidified with sulfuric acid so the calcium ions are precipitated as gypsum. The free sugars, protein, and acetic acid (HOAc) will be concentrated by an appropriate technology (e.g reverse osmosis or multi-effect evaporation). It may be sold as monogastric (e.g. chickens, pigs) animal feed.

The treated biomass will emerge from the process in a wet state. If the ruminant animals are located close to the processing plant, they may eat it directly in the wet state. If it must be stored for awhile before it is consumed, it may be dried in the steam driers we have previously described in past disclosures.

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hereto.

We claim:

1. A method for recovering calcium from a biomass pretreatment process comprising:

a) pretreating the biomass by adding calcium oxide or hydroxide and water to the biomass to form a mixture and maintaining the mixture at ambient pressure and at greater than ambient temperature for a period of time sufficient to enhance susceptibility of the biomass to hydrolysis;

b) carbonating the pretreated biomass;

c) precipitating calcium carbonate or bicarbonate from the carbonated biomass; and d) recovering precipitated calcium carbonate or bicarbonate.

2. The method of claim 1 wherein the mixture contains between about 6 to about 19 grams of water per gram of dry biomass.

3. The method of claim 1 wherein the mixture contains between about 9 to about 11 grams of water per gram of dry biomass.

4. The method of claim 1 wherein the mixture contains between about 2 to about 30 grams of calcium oxide or hydroxide per 100 grams of dry biomass.

5. The method of claim 1 wherein the mixture contains between about 10 to about 15 grams of calcium oxide or hydroxide per 100 grams of dry biomass.

6. The method of claim 1 wherein the lignocellulose-containing biomass is selected from the group consisting of grass, wood, bagasse, straw, paper, plant material, and combinations thereof.

7. The method of claim 1 wherein the mixture is maintained at the temperature of between about 40° C. to about 100° C.

8. The method of claim 1 wherein the mixture is maintained at the temperature of between about 40° C. and about 70° C.

9. The method of claim 1 wherein the mixture is maintained at the temperature of between about 50° C. and about 65° C.

10. The method of claim 1 wherein the mixture is maintained at the temperature of between about 70° C. and about 100° C.

11. The method of claim 1 wherein the period of time is between about 1 and about 36 hours.

12. The method of claim 1 wherein the period of time is between about 1 and about 20 hours.

13. The method of claim 1 wherein the period of time is between about 15 and about 25 hours.

14. The method of claim 1 wherein the period of time is about 24 hours.

15. The method of claim 1 wherein the period of time is between about 1 and about 2 hours.

16. The method of claim 1 wherein the mixture is maintained at a temperature of between about 40° C. and about 100° C., and the period of time is between about 1 and about 36 hours.

17. The method of claim 1 wherein lignin content of the biomass is reduced between about 10% to about 20% by pretreatment.

18. The method of claim 1 wherein the pH of the carbonated biomass is between about 8.5 and about 10.5.

19. The method of claim 1 wherein the pH of the carbonated biomass is between about 9.0 and about 10.

20. The method of claim 1 wherein the recovered calcium oxide is hydrated to form calcium hydroxide.

21. The method of claim 1 further comprising heating the carbonated biomass to form carbon dioxide and calcium oxide.

22. The method of claim 21 wherein the precipitated calcium oxide is recovered by filtration, hydroclone separation, sedimentation, centrifugation, or a combination thereof.

23. A method for recovering calcium from a biomass pretreatment process comprising:

a) pretreating the biomass by adding calcium oxide or hydroxide and water to the biomass to form a mixture and maintaining the mixture at ambient pressure and at greater than ambient temperature for a period of time sufficient to enhance susceptibility of the biomass to hydrolysis;

b) adding a carbonating agent to the pretreated mixture to form calcium carbonate or bicarbonate;

c) heating the calcium carbonate or bicarbonate to form calcium oxide; and recovering the calcium oxide.

24. The method of claim 23 wherein lignin content of the biomass is reduced between about 10% to about 20% by pretreatment.

25. The method of claim 23 wherein the carbonating agent is carbon dioxide gas.

26. The method of claim 23 wherein said pretreated mixture contains lignin and wherein the lignin is burned to heat the calcium carbonate or bicarbonate of step b.

27. The method of claim 23 further comprising the step of digesting the carbonated mixture.

28. The method of claim 27 wherein digestion is performed by acid hydrolysis, enzymatic action, fermentation or a combination thereof.

29. The method of claim 23 wherein the mixture is dry mixed before pretreatment.

30. The method of claim 23 wherein the mixture is continuously mixed during pretreatment.

* * * * *